US007741024B2

(12) United States Patent
Wyatt et al.

(10) Patent No.: US 7,741,024 B2
(45) Date of Patent: Jun. 22, 2010

(54) IMMUNOGENIC PROTEOLIPOSOMES, AND USES THEREOF

(75) Inventors: Richard T Wyatt, Rockville, MD (US); Joseph G Sodroski, Medford, MA (US); Tajib Mirzabekov, Palo Alto, CA (US); Christoph Grundner, Oakland, CA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 268 days.

(21) Appl. No.: 11/781,998

(22) Filed: Jul. 24, 2007

(65) Prior Publication Data

US 2007/0292436 A1    Dec. 20, 2007

Related U.S. Application Data

(62) Division of application No. 10/450,637, filed as application No. PCT/US01/50820 on Dec. 27, 2001, now Pat. No. 7,276,579.

(60) Provisional application No. 60/258,438, filed on Dec. 27, 2000.

(51) Int. Cl.
*C12Q 1/70* (2006.01)
*G01N 33/53* (2006.01)

(52) U.S. Cl. .................. 435/5; 435/7.1; 502/4; 502/7

(58) Field of Classification Search ........................ None
See application file for complete search history.

(56) References Cited

U.S. PATENT DOCUMENTS 5,766,625 A * 6/1998 Schreier et al. ............. 424/450
5,817,316 A   10/1998 Sodroski
5,858,366 A   1/1999 Sodroski
6,761,902 B2 * 7/2004 Sodroski et al. ............ 424/450

FOREIGN PATENT DOCUMENTS

WO   WO 99/16883 A2   4/1999
WO   WO 01/19958 A3   3/2001
WO   WO 01/49265 A1   7/2001

OTHER PUBLICATIONS

Alkhatib, G., et al., Science 272:1955-1958 (1996).
Allan, JS., et al., Science 228:1091-1093 (1985).
Barré-Sinoussi, F., et al., Science 220:868-871 (1983).
Berman, PW., et al., J. Infect. Dis. 176:384-97 (1997).
Broder, C.C., et al., Proc. Natl. acad. Sci USA 91:11699-703 (1994).
Bullough, P., et al., Nature 371:37-43 (1994).
Burton, D. R. and D. C. Montefiori, AIDS 11 Suppl. A: S87-98 (1997).
Burton, D. R. and J. P. Moore, Nature Med. 4 (5 Suppl.) 495-8 (1998).
Cao, J., et al., J. Virol. 67:2747-55 (1993).
Carr, CM., et al., Cell 73:823-832 (1993).
Chan, DC., et al., Cell 89:263-273 (1997).
Choe, H., et al., Cell 85:1135-1148 (1996).
Choe, H., et al., Semin. Immunol. 10:249-57 (1998).
Connor, R. I., et al., J. Virol. 72:1552-76 (1998).
Dalgleish, AG., et al., Nature 312:763-767 (1984).
Deng, HK., et al., Nature 381:661-666 (1996).
Doranz, BJ., et al., Cell 85:1149-1158 (1996).
Dragic, T., et al., Nature 381:667-673 (1996).
Earl, PL., et al., J. Virol. 65:2047-2055 (1991).
Farzan, M., et al., J. Virol. 72:7620-5 (1998).
Fauci, A. S., et al., Ann Intern Med 100: 92-106 (1984).
Federsppiel et al., Genomics 16:707-712, 1993.
Feng, Y., et al., Science 272:872-877 (1996).
Freed, E.O., et al., Proc. Natl. Acad. Sci. USA 87:4650-4 (1990).
Gallo, RC., et al., Science 224:500-503 (1984).
Helseth, E., et al., J. Virol. 65:2119-23 (1991).
Helseth, E., et al., J. Virol. 64:6314-8 (1990).
Hill, C. P., et al., Proc. Natl. Acad. Sci. USA 93:3099-3104 (1996).
Jazin et al., Regulatory Peptides 47:247-258, 1993.
Klatzmann, D., et al., Nature 312:767-8 (1984).
Kowalski, M., et al., Science 237:1351-1355 (1987).
Loetscher et al., J Bio Chem 269(1):232-237, 1994.
Mascola, J. R., et al., J. Infect. Dis. 173:340-8 (1996).
McDougal, J. S., et al., J. Immunol. 137:2937-44 (1986).
McKeating, J. A., et al., J. Virol. 65:852-60 (1991).
Mirzabekov et al., J. Biol. Chem., 274:28745-50 (1999).
Montefiori, D. C. and Evans, T. G., AIDS Res. Human Retroviruses 15:689-98 (1999).
Moore, J. P. et al., J. Virol. 69:101-109 (1995).
Moore, J. P. and Sodroski, J., J. Virol. 70:1863-1872 (1996).
Moore, J. P., et al., J. Virol. 68:469-484 (1994).
Parren, P. W. H. I. and Burton, D. R., Nature Med. 3:366-7 (1997).
Parren, P. W. H. I., et al., J. Virol. 72: 3512-9 (1998).
Rao, Z., et al., Nature 378:743-7 (1995).
Robey, WG., et al., Science 228:593-595 (1985).
Tan, K., et al., Proc. Natl. Acad. Sci. USA 94:12303-8 (1997).
Veronese, F. D., et al., Science 229:1402-1405 (1985).

(Continued)

Primary Examiner—Mary E Mosher
Assistant Examiner—Myron G Hill
(74) Attorney, Agent, or Firm—Fish & Richardson P.C.

(57) ABSTRACT

An immunogenic proteoliposome containing a transmembrane protein or oligomeric complexes containing such proteins, including viral envelope glycoproteins, in a lipid membrane around an elliptoid or spherical shape. The shape preferably also contains an attractant such as streptavidin or avidin and the lipid membrane contains a moiety that binds to the attractant such as biotin. The immunogenic transmembrane protein is bound to a ligand which is anchored in the shape. Methods for making the immunogenic proteoliposomes are provided. uses of the proteoliposome are described, including their use as immunogens to elicit immune reaction, and their use in screening assays, including their use as antigens to screen antibody libraries, as well as for drug screening and the identification of ligands.

8 Claims, 18 Drawing Sheets

OTHER PUBLICATIONS

Wyatt, R., et al., J. Virol. 71:9722-31 (1997).
Wyatt, R., and J. Sodroski, Science 280:1884-8 (1998).
Grundner, C. et al., J Virol. 76(7):3511-3521, 2002.
Grundner, C. et al., Virology 331(1):33-46, 2005.
Moulard, M. et al., J Virol. 74(4):1948-1960, 2000.
Yang, X. et al., J Virol. 76(9):4634-4642, 2002.
Yang, X. et al., J Virol. 75(3):1165-1171, 2001.
Yang, X. et al., J Virol. 74(10):4746-4754, 2000.
Yang, X. et al., J Virol. 74(12):5716-5725, 2000.
Weissenhorn, W., et al., Nature 387:426-430 (1997).
Weissenhorn, W., et al., Proc. Natl. Acad. Sci. USA 95:6032-6 (1998).
Weissenhorn, W., et al., Mol. Cell 2:605-16 (1998).
Willey et al., J. Virol. 68:1029-39 (1994).

* cited by examiner

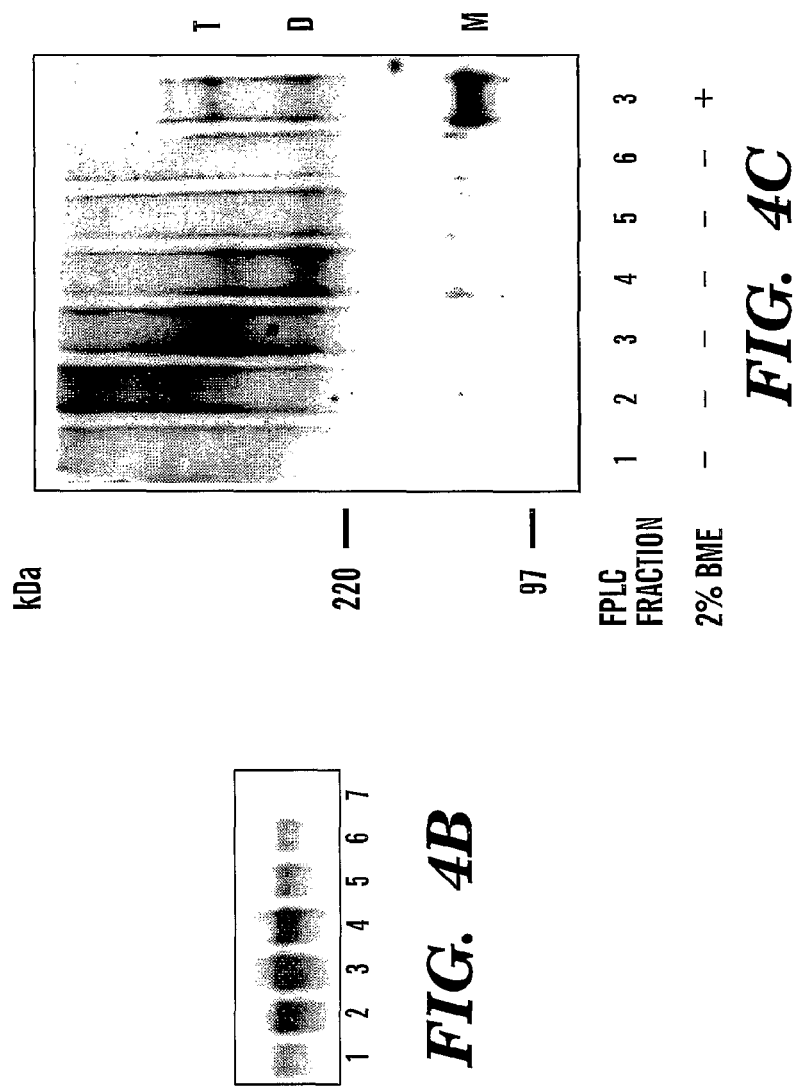
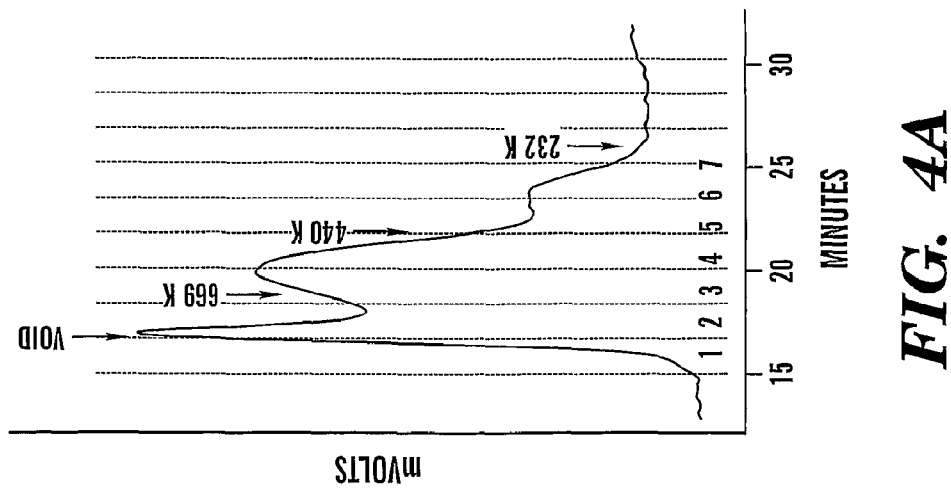
FIG. 4A  FIG. 4B  FIG. 4C

IMMUNOGENIC PROTEOLIPOSOMES, AND USES THEREOF

This application is a divisional under 35 U.S.C. §120 of U.S. application Ser. No. 10/450,637, filed Dec. 17, 2003, now U.S. Pat. No. 7,276,579, which is a U.S. National Phase Entry under 35 U.S.C. §371 of International Application No. PCT/US2001/50820, filed Dec. 27, 2001, which designated the U.S. and which claims the benefit under 35 U.S.C. §119 (e) of U.S. Provisional Application Ser. No. 60/258,438, filed Dec. 27, 2000, which applications are incorporated herein by reference.

This invention was supported by National Institutes of Health Grant AI41851 and the government of the United States has certain rights thereto.

FIELD OF THE INVENTION

The present invention is directed to immunogenic proteoliposomes, particularly those containing envelope glycoproteins, their construction and use. Preferably the proteoliposome contains a lentiviral envelope protein. Preferably the proteoliposomes are used to elicit an immunogenic response or screen for ligands, including antibodies, small molecules, and proteins.

BACKGROUND OF THE INVENTION

Proteins that are present on the surface of a cell or virus are typically transmembrane proteins. These proteins include cell surface receptors and envelope glycoproteins, and these proteins are involved in a variety of protein to protein interactions. For example, as demonstrated with pseudotyped viral particles, the specific envelope protein present on a viral surface determines the receptor that the virus will bind to. Additionally, the three dimensional conformation of the protein has an important effect on the particular interaction. However, maintaining a desired conformation can be difficult. For example, many receptors, envelope proteins, etc. are the result of multimeric formation of individual monomers. Thus, even though each subunit may span the membrane only once, the multimeric complex has several membrane-spanning components that could contribute to its overall conformational integrity.

Significant attention has been focused on viruses including the flu virus, herpes virus, retroviruses, lentiviruses, etc., particularly in the mechanism of infection. Human immunodeficiency virus type 1 (HIV-1) and type 2 (HIV-2) are the etiologic agents of acquired immunodeficiency syndrome (AIDS), which results from the profound depletion of CD4-positive lymphocytes in infected individuals (Barre-Sinoussi, F., et al., *Science* 220:868-71, 1983; Gallo, R. C., et al., *Science* 224: 500-3, 1984; Fauci, A. S., et al., *Ann Intern Med* 100: 92-106, 1984).

Though great progress has been made in the treatment of individuals infected with viruses such as HIV, numerous problems still remain. For example, treatment typically requires taking cocktails of medicines at different times over extended periods of time. The failure to do so can result in seriously undermining the treatment, and ultimately results in further progression of the disease. Even where individuals follow the treatment protocol, there are many instances of disease progression. Moreover, the treatment is extremely costly, effectively rendering it out of reach to many individuals in the United States, and in much of the rest of the world. There are also other viruses for which antiviral therapy has not yet been developed.

Accordingly, the development of alternative methods of dealing with viral infection, such as HIV infection, is still extremely important.

One area where a great deal of attention has been extended has been in utilizing viral sub-units to generate immune reactions. Antibodies that neutralize viruses typically do so by inhibiting viral binding to surface receptors. The major protein found on the surface of HIV, and therefore a major target for generating neutralizing antibodies, is the envelope glycoprotein, gp120. This protein appears on the surface of the virion, thus rendering it a prime target for the immune system.

Unfortunately, the HIV-1 envelope glycoproteins have proven inefficient in generating antibodies that neutralize the virus, especially those that can neutralize more than a limited number of HIV-1 strains (Berman, P. W., et al., *J. Infect. Dis.* 176: 384-97, 1997; Connor, R. I., et al., *J. Virol.* 72: 1552-76, 1998; Mascola, J. R., et al., *J Infect. Dis.* 173: 340-8, 1996; reviewed in Burton, D. R. and D. C. Montefiori, *AIDS* 11 Suppl. A: S87-98, 1997; Burton, D. R. and J. P. Moore, *Nature Med.* 4(5 Suppl.) 495-8, 1998; and Wyatt, R. and J. Sodroski, *Science* 280: 1884-8, 1998). Many of the antibodies elicited by the envelope glycoproteins are not able to bind efficiently to the functional envelope glycoprotein trimer and therefore are devoid of neutralizing activity (Broder, C. C., et al., *Proc. Natl. Acad. Sci. USA* 91: 11699-703, 1994; Moore, J. P., et al., *J. Virol.* 69: 101-9, 1995; Moore, J. P., et al., *J. Virol.* 70: 1863-72, 1996; Parren, P. W., et al., *Nature Med.* 3:366-7. 1997; Parren, P. W., et al., *J. Virol.* 72: 3512-9, 1998; Wyatt, R., et al., *J. Virol.* 71: 9722-31, 1997). The lability of the envelope glycoprotein trimers, conformational flexibility in the shed gp120 glycoprotein, and the variability and glycosylation of the gp120 surface all appear to contribute to the poor neutralizing antibody responses (reviewed in Montefiori, D. C., et al., *AIDS Res. Human Retroviruses* 15: 689-98, 1999; Moore, J., et al., *J. Virol.* 68: 469-84, 1995; and Wyatt, R., and J. Sodroski, *Science* 280: 1884-8, 1998).

The entry of primate lentiviruses such as HIV-1 and HIV-2 into target cells is mediated by the viral envelope glycoproteins (Wyatt, R., and J. Sodroski, *Science* 280: 1884-8, 1998). The mature envelope glycoproteins on the primate lentivirus are organized into an external gp120 (gp125 for HIV-2) exterior envelope glycoprotein and the gp41 transmembrane envelope glycoprotein (gp36 for HIV-2) (Alan, J. S., et al., *Science* 228: 1091-4, 1985; Earl, P. L., et al., *J. Virol.* 65: 2047-55, 1991; Robey, W. G., et al., *Science* 228: 593-595, 1985; Veronese, F. D., et al., *Science* 229: 1402-1405, 1985; Wyatt, R., and J. Sodroski, *Science* 280: 1884-8, 1998). For example, in the infected cell, the HIV-1 envelope glycoprotein is initially synthesized as an 845- to 870-amino acid protein, depending upon the viral strain (Earl, P. L., et al., *J. Virol.* 65: 2047-2055, 1991). N-linked, high-mannose sugars are added to this primary translation product to result in the gp160 envelope glycoprotein precursor (gp140 for HIV-2). Oligomers of gp160 form in the endoplasmic reticulum, and several pieces of evidence suggest that these are trimers. First, X-ray crystallographic studies of fragments of the gp41 ectodomain revealed the presence of very stable, six-helix bundles (Chan, D. C., et al., *Cell* 89: 263-73, 1997; Tan, K., et al., *Proc. Natl. Acad. Sci. USA* 94: 12303-8, 1997; Weissenhom, W., et al., *Nature* 387: 426-30, 1997). These structures were composed of a trimeric coiled coil involving N-terminal gp41 α helices, with three C-terminal gp41 α helices packed into the grooves formed by the three inner helices. Second, introduction of cysteine pairs at specific locations in the coiled coil resulted in the formation of intermolecular disulfide bonds between the gp160 subunits (Farzan, M., et al., *J. Virol.* 72: 7620-5, 1998). The disulfide-stabilized oligomer was shown to be a trimer. Finally, the matrix proteins of HIV-1 and the related simian immunodeficiency viruses, which interact with the intravirion domains of the envelope glycoproteins, crystallize as trimers (Hill, C. P., et al., *Proc. Natl. Acad. Sci. USA* 93: 3099-3104, 1996; Rao, Z., et al., *Nature* 378: 743-7, 1995).

Following oligomerization, the precursor glycoprotein is transported to the Golgi apparatus, where cleavage by a cellular protease generates the external protein, gp120, and the trans-membrane protein, gp41 (Alan, J. S., et al., *Science* 228: 1091-4, 1985; Robey, W. G., et al., *Science* 228: 593-595, 1985; Veronese, F. D., et al., *Science* 229: 1402-1405, 1985). The gp120 glycoprotein remains associated with the gp41 glycoprotein through non-covalent, hydrophobic interactions (Helseth, E., et al., *J. Virol.* 65:2119-23, 1991; Kowalski, M., et al., *Science* 237: 1351-1355, 1987). The lability of the gp120-gp41 association results in the "shedding" of some gp120 molecules from the trimer, resulting in non-functional envelope glycoproteins (McKeating, J. A., et al., *J. Virol.* 65: 852-60, 1991; Willey et al., *J. Virol.* 68: 1029-39, 1994). It has been suggested that these disassembled envelope glycoproteins result in the generation of high titers of non-neutralizing antibodies during natural HIV-1 infection (Burton, D. R., and J. P. Moore, *Nat. Med.* 4 (5 Suppl.): 495-8, 1998; Moore, J. P., and J. Sodroski, *J. Virol.* 70 1863-72, 1996; Parren, P. W., et al., *J. Virol.* 72: 3512-9). The envelope glycoprotein trimers that remain intact undergo modification of a subset of the carbohydrate moieties to complex forms before transport to the cell surface (Earl, P. L., et al., *J. Virol.* 65: 2047-55, 1991).

The mature envelope glycoprotein complex is incorporated from the cell surface into virions, where it mediates virus entry into the host cell. The gp120 exterior envelope glycoprotein binds the CD4 glycoprotein, which serves as a receptor for the virus (Dalgleish, A. G., et al., *Nature* 312: 763-7, 1984; Klatzmann, D., et al., *Nature* 312: 767-8, 1984; McDougal, J. S., et al., *J. Immunol.* 137: 2937-44, 1986). Binding to CD4 induces conformational changes in the envelope glycoproteins that allow gp120 to interact with one of the chemokine receptors, typically CCR5 or CXCR4 (Alkhatib, G., et al., *Science* 272: 1955-8, 1996; Choe, H., et al., *Cell* 85: 1135-48, 1996; Deng, H., et al., *Nature* 381: 661-6, 1996; Doranz, B. J., et al., *Cell* 85: 1149-58, 1996; Dragic, T., et al., *Nature* 381: 667-73, 1996; Feng, Y., et al., *Science* 272: 872-7, 1996; reviewed in Choe, H., et al., *Semin. Immunol.* 10: 249-57, 1998). The chemokine receptors are seven-transmembrane, G protein-coupled receptors, and gp120 interaction with the chemokine receptors is believed to bring the viral envelope glycoprotein complex nearer to the target cell membrane and to trigger additional conformational changes in the envelope glycoproteins. Although the exact nature of these changes is unknown, mutagenic data are consistent with a role for the hydrophobic gp41 amino terminus (the "fusion peptide") in mediating membrane fusion (Cao, J., et al., *J. Virol.* 67: 2747-55, 1993; Freed, E. O., et al., *Proc. Natl. Acad. Sci. USA* 87: 4650-4, 1990; Helseth, E., et al., *J. Virol.* 64: 6314-8, 1990; Kowalski, M., et al., *Science* 237: 1351-5, 1987). It has been suggested that, following interaction of the "fusion peptide" with the target cell membrane, formation of the six-helical bundle by the three gp41 ectodomains would result in the spatial juxtaposition of the viral and target cell membranes (Chan, D. C., et al., *Cell* 89: 263-73, 1997). Six-helical bundles have been documented in several viral envelope glycoproteins that mediate membrane fusion and virus entry (Bullough, P. A., et al., *Nature* 371: 37-43, 1994; Carr, C. M., and P. S. Kim, *Cell* 73: 823-32, 1993; Weissenhorn, W., et al., *Proc. Natl. Acad. Sci. USA* 95: 6032-6, 1998; Weissenhorn, W., et al., *Mol. Cell* 2: 605-16, 1998). The formation of this energetically stable structure from a different and as-yet-unknown precursor structure is believed to provide the energy necessary to overcome the repulsion between the viral and cell membranes.

Initial attempts to generate immune reactions to HIV envelope glycoproteins have encountered substantial difficulties. For example, it was discovered that there are numerous regions in the glycoprotein which rapidly mutate in response to antibodies or drugs directed thereto. These regions also vary significantly from one strain of HIV to another. Accordingly, these regions have been described as variable regions. There are other regions that are conserved among HIV-1, HIV-2 and SIV strains. Variable regions and conserved regions of gp120 have been mapped and are well known in the art. In the three-dimensional structure of the protein, these variable regions are typically at the surface, and thus mask the more conserved regions. The variable regions are highly antigenic, typically generating most of the antibodies seen. It is only late in the progression of the disease that antibodies generated to the conserved regions are typically seen. Such antibodies include the F105 antibody, the 17b antibody and the 48d antibodies. The amino acids comprising the epitopes for these antibodies are proximal to each other in the three-dimensional structure of the protein, but appear distant from each other when one looks strictly at a one-dimensional linear amino acid sequence. Such an epitope is referred to as a discontinuous conformational epitope. Furthermore, the amino acids comprising these discontinuous conformational epitopes are located in a number of conserved regions. Numerous variable-region deleted glycoproteins that expose these discontinuous conformational epitopes by deleting portions of the variable regions are disclosed in U.S. Pat. Nos. 5,817,316 and 5,858,366.

Consequently, it is clear that the three-dimensional structure of the protein is extremely important in terms of what the immune system actually sees. Unfortunately, the individual monomers like other multimeric proteins do not typically form a stable multimer, in this case trimeric spikes, that approximate the natural wild type confirmation. Thus, generating neutralizing antibodies depends upon stabilizing the three-dimensional, trimeric structure of the envelope glycoprotein.

Attempts have been made to stabilize trimers by stabilizing interactions in the gp41 segment, for example by introducing cysteine residues. Another approach has been by inserting coiled coils in a portion of the transmembrane protein such as for HIV-1, gp41 or for HIV-2, gp36. Given the importance of being able to make and use such stable multimers, it is very desirable to have new methods for preparing such stable trimers. Particularly so if one wants to use such multimers to elicit an immune response.

The ability to create new in vitro assays to screen for molecules that can interact with a stable multimer such as the envelope glycoprotein is extremely important.

The G protein-coupled seven transmembrane segment receptor CXCR4, previously called HUMSTR, LCR-1 or LESTR (Federsppiel et al., 1993; Jazin et al., 1993; Loetscher et al., 1994) has been shown to allow a range of non-human, CD4-expressing cells to support infection and cell fusion mediated by laboratory-adapted HIV-1 envelope glycoproteins (Feng et al., 1996). Other G-protein-coupled seven transmembrane segment receptors such as CCR5, CCR3 and CCR2 have been shown to assist cellular entry of other HIV-1 isolates. It is believed that the cellular entry occurs as a result of the interaction of the external envelope glycoprotein, e.g., gp120, CD4 and the chemokine receptor. This further illustrates the importance of having an in vitro screen for testing molecules that more closely approximates the wild type env to determine their effect on the external env. Thus, the ability to express the envelope glycoprotein with its three-dimensional structure is extremely important in terms of what the immune system actually sees.

One of the particular challenges in expressing the env protein with its wild type conformation is that it is a transmembrane protein. Transmembrane proteins or integral membrane proteins are amphipathic, having hydrophobic domains that pass through the membrane and interact with the hydrophobic lipid molecules in the interior of the bilayer, and hydrophilic domains which are exposed to the aqueous environment on both sides of the membrane (for example, the aqueous environments inside and outside of the cell). The biological activities of integral membrane proteins (e.g., ligand binding) can be dependent upon the hydrophilic domains; in some cases, the membrane—spanning regions contribute to function.

It would be desirable to produce, isolate and stabilize in purified form while retaining their wild-type conformation transmembrane proteins, particularly multimeric proteins, such as gp120, and oligomeric complexes of transmembrane proteins such as gp120/CD4 and gp120/CD4/CCR5. It would be desirable if these proteins could be maintained in their wild-type conformation for extended periods of time and under conditions commonly found in vivo. The purification of transmembrane proteins, including oligomeric complexes, in a functionally relevant conformation should expedite the ability to elicit immune reactions to epitopes specifically exposed when the protein(s) is in its the wild-type conformation or in an oligomeric complex, as well as expedite their use in screening assays to identify antibodies, ligands, and small molecules that bind the transmembrane protein(s).

SUMMARY OF THE INVENTION

We have now discovered a method for expressing, while maintaining in a wild-type conformation for extended periods of time, transmembrane proteins and oligomeric complexes containing such proteins by formation of proteoliposomes. Preferably, the proteins are envelope proteins. Still more preferably, the proteins are lentiviral proteins.

The lentiviral protein is preferably from a primate lentivirus, still more preferably a human immunodeficiency virus (HIV-1), e.g. the HIV-1 gp120 or HIV-1 gp160.

Oligomeric complexes containing lentiviral proteins can include any lentiviral proteins and any proteins which bind lentiviral proteins.

Preferably, the proteoliposome contains the purified lentiviral envelope protein, such as gp120 or gp160. The oligomeric form is a trimer as discussed above. In another preferred embodiment, the proteoliposome contains the lentiviral envelope glycoprotein and a cellular receptor such as CD4. In a further embodiment, the proteoliposome contains the lentiviral envelope glycoprotein, CD4, and a chemokine receptor, such as CCR5 or CXCR4.

The proteins expressed in the proteoliposomes are extended by a short peptide epitope tag, for example the C9 tag, which can be recognized by an antibody (for example, the 1D4 antibody). The tag can be added to the N-terminus or to the C-terminus of the protein, depending upon the ultimate orientation of the protein in the proteoliposome that is desired. When multiple proteins are expressed in the same proteoliposome, they can contain the same or different epitope tags. The desired protein is expressed in a cell. Codon optimization may be used to increase the expression level of the protein. The protein is then isolated from the cell by a solubilizing agent that maintains the protein's conformation. Preferably, the solubilizing agent is a detergent. Preferred detergents include alkyl glucopyranosides (such as C8CP, C10-M, C12-M, Cymal-5, Cymal-6 and Cymal-7), alkyl sucroses (such as HECAMEG), digitonin, CHAPSO, hydroxyethylglucamides (such as HEGA-10), oligoethyleneglycol derivatives (such as C8ES, $C8E_n$ and C12E8), dodecylmaltopyranoside, and phenyl polyoxethylenes (such as Triton X-100).

The detergent-solubilized proteins are then separated from the other cellular debris by capture onto a solid surface (e.g. a spherical or ellipsoid bead). The bead has on its surface an antibody or other specific ligand that will capture, orient and concentrate the protein on the surface of the bead. When multiple proteins are expressed in the same proteoliposome, the bead can contain the same or different antibodies to capture, orient and concentrate each protein on the surface of the bead. The isolated protein is maintained in its wild-type conformation. Thereafter, it is mixed with a lipid component. Preferably, it also has an attractant for the lipid. For example, the bead can be streptavidin-coated and some lipid component (e.g. biotinyl-DPPE) can be covalently conjugated to biotin. The bead with the mixture is then subjected to a known means such as dialysis to form the proteoliposome. The streptavidin-biotin interaction, in this example, helps maintain the lipid layer as the detergent is removed. The resulting proteoliposome will maintain the integral membrane protein in its native conformation in an isolated and/or purified form for extended periods of times.

These proteoliposomes can be used as immunogens to elicit immune reactions. Alternatively, they can be used to screen antibody libraries for an antibody. In a preferred embodiment, the stable multimeric proteoliposomes can be used as antigens to screen phage display antibody libraries. Preferably, the immunogenic proteoliposome contains the purified lentiviral envelope protein, such as gp120 or gp160.

In another preferred embodiment, the immunogenic proteoliposome contains the lentiviral envelope glycoprotein and a cellular receptor such as CD4.

In a further preferred embodiment, the immunogenic proteoliposome contains the lentiviral envelope glycoprotein, CD4, and a chemokine receptor, such as CCR5 or CXCR4.

In another preferred embodiment, the immunogenic proteoliposome contains molecules that can enhance immune responses, for example, costimulatory molecules such as B7-1 or B7-2. It can also contain costimulatory molecules such as LFA-1, ICAM, GM-CSF, or cytokines such as interleukins or interferons. It can also contain multiple costimulatory molecules.

These proteoliposomes can also be used in screening assays such as drug screening and identifying ligands. In another preferred embodiment, the antigenic proteoliposome contains the lentiviral envelope glycoprotein and a cellular receptor such as CD4. Preferably, the antigenic proteoliposome contains the purified lentiviral envelope protein, such as gp120 or gp160. In a further preferred embodiment, the antigenic proteoliposome contains the lentiviral envelope glycoprotein, CD4, and a chemokine receptor, such as CCR5 or CXCR4.

These proteoliposomes can also be used to determine the protein's structure.

These proteoliposomes can also be used as a vaccine.

BRIEF DESCRIPTION OF THE DRAWINGS

FIG. 2A shows an SDS-PAGE gel of gp160ΔCT glycoproteins eluted from 5×10⁷ PLs, stained with Coomassie blue. Lane 1 shows 1 μg of affinity-purified gp160, lane 2 shows protein eluted from gp160ΔCT PLs and lane 3 shows protein eluted from beads conjugated with the 1D4 antibody. FIG. 2B shows FACS analysis of PLs stained with the IgGb12 antibody (peak 2) and HIV-1 patient serum (peak 3), compared to anti-human FITC secondary antibody alone (peak 1).

FIG. 3A shows autofluorescence. FIG. 3B shows gp160 proteoliposomes reconstituted with a lipid preparation containing 1% DOPE-Rhodamine.

FIGS. 4A-C show size exclusion chromatography and Western blot of JR-FL gp160ΔCT glycoproteins eluted from Dynal beads under native conditions. 293T cells transiently expressing the JR-FL gp160ΔCT C9-tagged glycoproteins were lysed in CHAPS containing buffer and incubated with Dynal beads conjugated with the 1D4 antibody. Beads were then washed and incubated in buffer containing 0.2 mM C9 peptide and 0.5 M MgCl$_2$ to elute the gp160ΔCT glycoprotein from the beads. In FIG. 4A, approximately 5 μg of JR-FL gp160ΔCT glycoproteins were analyzed on a Superdex-200 gel filtration column. In FIG. 4B, eluted fractions were collected, analyzed by SDS-PAGE under reducing conditions (2% BME) and analyzed by Western blot with a polyclonal anti-gp120 rabbit serum. In FIG. 4C, eluted fractions were analyzed on a 3-8% SDS-PAGE gradient gel under non-reducing conditions, and under reducing conditions (2% BME), respectively, and detected by Western blotting using a polyclonal anti-gp120 rabbit serum. Protein bands of apparent molecular weights consistent with trimeric gp160ΔCT glycoproteins (T), dimeric glycoproteins (D) and monomeric glycoproteins (M) are marked as indicated.

FIG. 5A shows occlusion of the 1D4 antibody by lipid membrane reconstitution. gp160ΔCT PLs with (peak 2) and without (peak 3) a reconstituted membrane were probed with anti-mouse Ig-PE antibody. Peak 1 shows staining with the same antibody of non-conjugated beads. In FIG. 5B, PLs with a reconstituted membrane containing 1% biotinylated lipid (peak 2) and beads without a reconstituted membrane (peak 1) were probed with Avidin-FITC.

FIG. 14A shows staining with polyclonal α-gp120 mouse serum and α-mouse-PE. FIG. 14B shows staining with bacterial medium containing phage/single-chain antibodies (1:2 dilution), α-phage mouse IgG and α-mousePE.

DETAILED DESCRIPTION OF THE INVENTION

Figure 1:
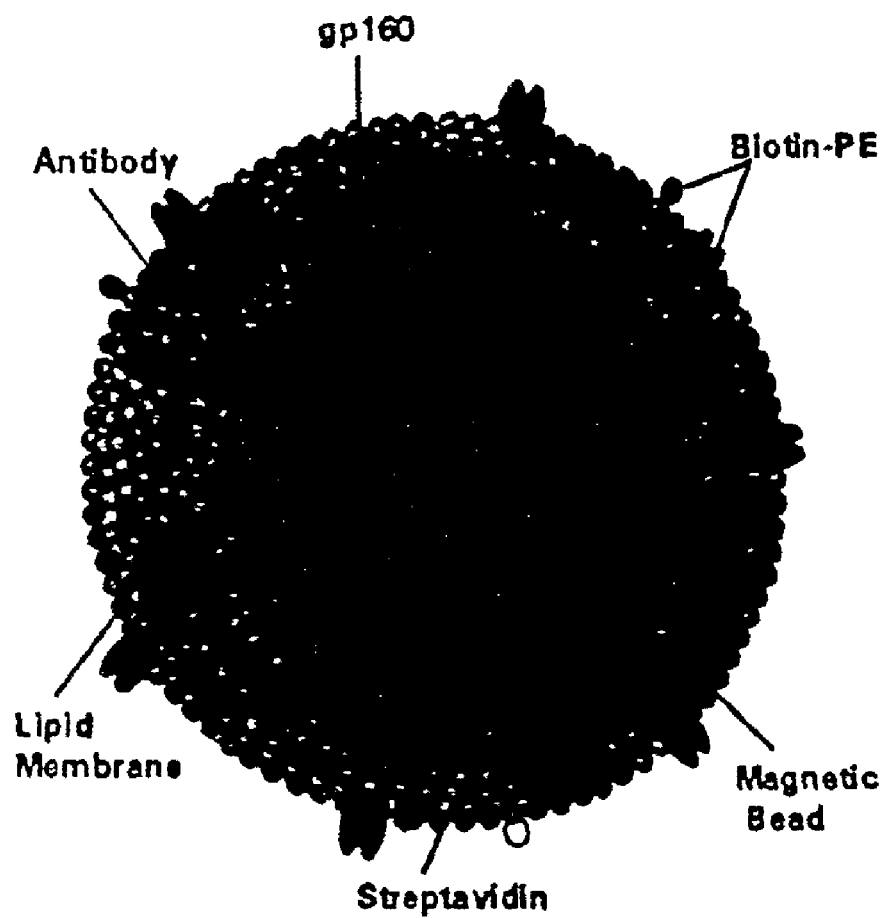
FIG. 1 shows a schematic representation of the reconstituted gp160 proteoliposomes.

We have now found a method for expressing transmembrane proteins and oligomeric complexes containing such transmembrane proteins in large amounts, purifying and isolating them from other proteins, while maintaining them in a wild-type conformation for extended periods of time. The protein of interest may be known to be a membrane protein or may be a putative membrane protein, based upon structure predictions from its distribution of hydrophobic amino acids.

Preferably, the transmembrane proteins are envelope proteins. Still more preferably, the proteins are lentiviral proteins. The lentiviral proteins can include, for example, proteins from human immunodeficiency virus (HIV), feline immunodeficiency virus (FIC), or visna virus. Preferably, the transmembrane protein is comprised of multimers of the basic unit, such as the trimeric spikes formed by HIV-1 or HIV-2 envelope proteins, namely gp160 which cleaves to gp41 and gp120 for HIV-1 and gp140 which cleaves to gp125 and gp35 for HIV-2.

The lentiviral protein is preferably from a primate lentivirus, still more preferably a human immunodeficiency virus (HIV-1), e.g. the HIV-1 gp120 or HIV-1 gp160.

Oligomeric complexes containing lentiviral proteins can include any lentiviral proteins and any proteins which bind lentiviral proteins. In another preferred embodiment, the proteoliposome contains the lentiviral envelope glycoprotein and a cellular receptor such as CD4. In a further embodiment, the proteoliposome contains the lentiviral envelope glycoprotein, CD4, and a chemokine receptor, such as CCR5 or CXCR4. In another preferred embodiment, the proteoliposome contains the lentiviral envelope glycoprotein and an immune stimulatory molecule such as B7-1 or B7-2.

As used herein, an extended period of time is at least 12 hours; preferably at least one day; still more preferably at least one week. Even more preferably an extended period of time is at least one month. Yet more preferably, at least two months.

Any method of expression may be used to express the desired transmembrane protein in a cell, prior to its purification by the present invention.

The list of transmembrane proteins, sometimes also referred to as integral membrane proteins, is vast. Transmembrane proteins may cross the membrane only once or over twenty times. Many transmembrane proteins associate with other transmembrane proteins to form larger complexes. Such complexes may be comprised of two identical subunits (such as homodimers) or two different protein subunits (such as heterodimers). There are examples of even larger complexes of three (sodium ion channel, $Na^+/K^+$ ATPase), four (aquaporin), five (cation channels of nicotinic receptors, anion channels of glycine receptors) or more (photoreaction center, mitochondrial respiratory chain) homologous or heterologous subunits.

Transmembrane proteins contribute to a wide variety of cellular functions, including the transport of molecules and ions into or out of cells, cell recognition, cell-to-cell communication, and cell adhesion. One simple way to classify transmembrane proteins is by their number of transmembrane domains (Table 1).

The group of transmembrane proteins that only cross the membrane once (also known as single-pass proteins) is particularly diverse both structurally and functionally. This class includes envelope glycoproteins and a large number of cell surface receptor proteins. For example, the EGF receptor binds epidermal growth factor, which leads to activation of the receptor's tyrosine kinase activity. Other examples of single-pass transmembrane proteins include the integrins and cadherins, which function in cell-cell communication via binding to extracellular molecules.

Other examples of viral envelope proteins include, for example, envelope proteins from filoviruses (such as Ebola virus), orthomyxoviruses (such as influenza virus), VSV-G, alpha viruses (such as Semliki forest virus and Sindbis virus), arena viruses (such as lymphocytic choriomeningitis virus), flaviviruses (such as tick-borne encephalitis virus and Dengue virus), rhabdoviruses (such as vesicular stomatitis virus and rabies virus), Moloney leukemia virus, HSV, VZV, Mumps virus, Rhinoviruses, Measles, Rubella, Arbovirus, Enteroviruses (such as Polio, Coxsackie, Echoviruses), Polio virus, Coxsackie B, A & Echovirus, Rhinoviruses, Hepatitis viruses, Norwalk virus, Astroviruses, Togavirus, Alphaviruses, Pestiviruses, Coronavirus, Parainfluenza, Mumps virus, Measles virus, Respiratory Syncytial Virus (RSV), Bunyaviridae, Reoviridue, Reoviruses, Rotaviruses, HTLV, Polyomaviruses, Papillomaviruses, Adenoviruses, Parvoviruses, EBV, CMV, Varicella Zoster virus, herpes viruses, and Pox viruses.

Another large class of cell surface receptors is the G-protein coupled receptors (GPCRs), which span the membrane seven times. Unlike many of the single-pass receptors, these proteins do not have enzymatic activity themselves but instead are functionally linked to signaling proteins known as G proteins. The chemokine receptor CCR5 that serves as the principal coreceptor for HIV-1 is a typical example of a G protein-coupled receptor.

Other well studied members of this class include transducin, which senses light, and the acetylcholine receptor, which binds neurotransmitter at neuronal synapses.

| Protein Class | Specific example | # TM domains | Reference |
| --- | --- | --- | --- |
| Receptor guanylyl cyclases | Sperm React receptor | 1 | MBOC pp. 759-60 |
| Receptor tyrosine kinases | EGF receptor | 1 | MBOC pp. 759-60 |
| Protein tyrosine phosphatases | CD45 | 1 | MBOC pp. 768 |
| Integrins | Alpha, beta chains | 1 | MBOC pp. 996-7 |
| Cadherins | E-cadherin | 1 | MBOC pp. 996-7 |
| Chemotaxis receptors | | 2 | MBOC pp. 775-6 |
| Some potassium channels | Kcs K channel | 2 | Doyle et al. |
| Connexins | | 4 | MBOC pp. 959 |
| Photosynthetic reaction center | L, M subunits | 5 | MBOC pp. 498 |
| Some ABC transporters | | 6 | Reimann & Ashcroft |
| Voltage-gated K+ channels | Shaker | 6 | Reimann & Ashcroft |
| G-coupled receptors | Transducin | 7 | |
| | Chemokine receptors | 7 | |
| | Acetylcholine receptor | 7 | |
| Ion pumps | Ca++ pump catalytic subunit | 10 | MBOC pp. 516 |
| | Na+—K+ pump catalytic sub. | 10 | MBOC pp. 516 |
| CIC channels | CIC-1 of skeletal muscle | 11 | Valverde |
| ABC transporters | MDR ATPase | 12 | MBOC pp. 522 |
| | Peptide pump | 12 | MBOC pp. 522 |
| | CFTR | 12 | MBOC pp. 522 |
| Anion transporters | Band 3 protein | 14 | MBOC pp. |

MBOC: Alberts, B., et al. (1998), Molecular Biology of the Cell, 3rd Edition, Garland Publishing, Inc., New York.
Doyle, D. A., et al. (1998), Science 280: 69-77.
Reimann, F., and Ashcroft, F. M. (1999), Cur. Op. Cell Biol. 11: 503-8.
Valverde, M. A. (1999), Cur. Op. Cell Biol. 11: 509-16.

Sequences of these proteins are widely available in the literature and from computer databases such as Genbank. Thus, one can readily obtain the gene encoding a particular protein of interest. This gene can be expressed by any known means. These include creating an expression cassette, where the gene is operably linked to a promoter. Other enhancing elements are known and may also be used. The codons used to synthesize the protein of interest may be optimized, converting them to codons that are preferentially used in mammalian cells. Optimal codons for expression of proteins in non-mammalian cells are also known, and can be used when the host cell is a non-mammalian cell (for example, insect cells, yeast cells, bacteria).

The gene is then introduced into a cell for the expression by known means. For example, they can include vectors, liposomes, naked DNA, adjuvant-assisted DNA, gene gun, catheters, etc. Vectors include chemical conjugates, plasmids, phage, etc. The vectors can be chromosomal, non-chromosomal or synthetic. Commercial expression vectors are well known in the art, for example pcDNA 3.1, pcDNA4 HisMax, pACH, pMT4, PND, etc. Promoters that can be used to express the gene are well known in the art. The promoter chosen are selected based upon the host cell which the protein is expressed in. These include cytomegalovirus (CMV) intermediate early promoter, a viral LTR such as the Rous sarcoma virus LTR, HIV-LTR, HTLV-1 LTR, the simian virus 40 (SV40) early promoter, E. coli lac V5 promoter and the herpes simplex TK virus promoter.

Preferred vectors include viral vectors, fusion proteins and chemical conjugates. Retroviral vectors include Moloney murine leukemia viruses. Other vectors include pox vectors such as orthopox or avipox vectors, herpesvirus vectors such as a herpes simplex I virus (HSV) vector (Geller, A. I. et al., (1995), *J Neurochem*, 64: 487; Lim, F., et al., (1995) in *DNA Cloning: Mammalian Systems*, D. Glover, Ed., Oxford Univ. Press, Oxford England; Geller, A. I. et al. (1993), *Proc. Natl. Acad. Sci.: U.S.A.* 90:7603; Geller, A. I., et al., (1990) *Proc Natl. Acad. Sci. USA* 87:1149), adenovirus vectors (LeGal LaSalle et al. (1993), *Science,* 259:988; Davidson, et al. (1993) *Nat. Genet* 3: 219; Yang, et al., (1995) *J. Virol.* 69: 2004) and adeno-associated virus vectors (Kaplitt, M. G., et al. (1994) *Nat. Genet.* 8: 148).

The particular vector chosen will depend upon the host cell used.

The introduction of the gene into the host cell can be by standard techniques, e.g. infection, transfection, transduction or transformation. Examples of modes of gene transfer include e.g., naked DNA, CaPO4 precipitation, DEAE dextran, electroporation, protoplast fusion, lipofection, cell microinjection, and viral vectors.

An antigenic tag may be inserted in the protein to assist in its purification and in orienting the protein on the solid surface. Preferably, the tag is present at either the N-terminal end or the C-terminal end of the protein. The tag is preferably 6 to 15 amino acids in length, still more preferably about 6 to 9 amino acids. The tag is selected and its coding sequence inserted into the gene encoding the protein in a manner not to affect the overall conformation or function of the protein. Tags can include HA, polyoma, C9, FLAG, etc.

The integral membrane protein expressing cell is then lysed in a buffer with the appropriate detergent and protease inhibitors so the protein can be separated from other cellular debris by conventional means without harming the protein.

In general, due to their amphipathic properties, transmembrane proteins can be solubilized only by agents that disrupt hydrophobic associations and destroy the membrane's lipid bilayer. The agents typically used are small amphipathic molecules which tend to form micelles in water. Preferably, the agent is a detergent. When mixed with membranes, the hydrophobic regions of the detergent bind to the transmembrane domain of proteins, displacing the lipid molecules. The polar ends of detergents can either be charged (ionic) or uncharged (non-ionic). Although integral membrane proteins can be maintained in a native conformation in a detergent solution, over time many such solubilized proteins undergo denaturation and aggregation.

When a detergent is removed from a transmembrane protein-detergent complex in the absence of phospholipid, the membrane protein molecules usually denature, aggregate and precipitate out of solution. If, however, the purified protein is mixed with phospholipid before the detergent is removed, the active protein can insert into the lipid bilayer formed by the phospholipids. In this manner, functionally active membrane proteins can be reconstituted from purified components. An integral membrane protein properly reconstituted into its native lipid environment is stable for extended periods of time.

Additionally, a critical factor for maintaining a functional conformation of a membrane protein during its purification is the choice of detergent used to solubilize the protein. The detergent best suited for a given membrane protein is typically determined empirically. If the protein has been investigated previously, the literature will indicate successful detergents. Moreover, one can rely upon the results obtained with related proteins to determine detergents that will be successful with other proteins. Thus, research on a related protein indicates the type of detergent most likely to extract the protein in an active form.

Detergents can be generally classed, depending upon the nature of their polar end, into three groups: non-ionic, zwitterionic, and ionic. Strong ionic detergents (such as SDS) can solubilize most membrane proteins, but tend to unfold the protein in the process, making them less useful for reconstituting active conformations. In general, milder non-ionic detergents are preferred.

Detergents recommended for gentle solubilization of membrane proteins include alkyl glucopyranosides (such as C8-GP and C9-GP), alkyl thio-glucopyranosides (such as C8-tGP, C10-M, C12-M, Cymal-5, Cymal-6, and Cymal-7), alkyl sucroses (such as HECAMEG), CHAPSO, digitonin, hydroxyethylglucamides (such as HEGA-10), oligoethyleneglycol derivatives (such as C8E5, C8En, and C12E8), dodecylmaltopyranoside, and phenyl polyoxyethylenes (such as Triton X-100).

Preferred detergents include alkyl thioglucopyranosides, dodecylmaltopypanoside and phenyl polyoxyethydenes. More preferably, Cymal-5, Cymal-6, Cymal-7, HEGA-10, digitonin, CHAPSO, dodecylmaltopyranoside, and Triton X-100. Still more preferably Cymal-5, Cymal-6, Cymal-7, and dodecylmaltopyranoside.

Commercial kits are also available to assist in choosing a detergent appropriate for a given membrane protein. For example, both Anatrace and Calbiochem offer a variety of kits containing mixtures of different detergents.

There are many known instances of detergents which have been successfully used to purify functionally active membrane proteins. For example, decylmaltoside was used to purify the $K^+$ channel (Ksc $K^+$) from *Streptomyces lividans*, allowing its structure to be determined by X-ray crystallography (Doyle et al., *Science* (1998) 280: 69-77). Cymal-5, Cymal-6, Cymal-7, and dodecylmaltopypanoside are preferred detergents for GCPRs, more preferably for chemokine receptors (Mirzabekov, T. et al. (1999), *J. Biol. Chem.* 274: 28745-50).

The cleared cell lysate containing all solubilized membrane proteins and other water-soluble cellular proteins can be separated from the other cellular debris by conventional means. For example using high speed centrifugation, such as 150,000×g. Antibodies directed against the epitope tag on the protein of interest are used to capture this protein from the cell lysate onto the solid support (e.g., beads). After binding of the solubilized integral membrane protein to the antibodies immobilized on the solid support, the solid support is washed. Thereafter the purified detergent-protein mixture is formed into a proteoliposome as described below.

The proteoliposome comprises a spherical or ellipsoid shape such as a bead or other pellet. Preferably, the bead or pellet is at least about 15% the size of a eukaryotic cell; still more preferably it is at least about 20% the size of such a cell; and even more preferably it is at least about 25% the size of such a cell. The shape is three-dimensional so that it can be coated on all sides. However, there can be substantial variability in the exact shape used. The exact shape chosen will depend upon the way the proteoliposome is being used. Thus, in some embodiments flakes are preferable to beads, e.g., as an immunogen, in others, a thicker ellipsoid can be preferable.

Any lipid or lipid mixture that supports membrane reconstitution can be used. Preferred lipids include 1-Palmitoyl-2-Oleoyl-sn-Glycero-3-Phosphocholine (POPC), 1-Palmitoyl-2-Oleoyl-sn-Glycero-3-Phosphoethanolamine (POPE), Dimyristoylphosphatidic acid (DMPA) and Cholesterol. Preferably a mixture of these lipids is used, for example at molar concentrations 45:25:20:10. The lipid mixture can be dried in a 2-ml polyethylene tube under a vacuum until all of the solvent is removed. PBS can be added to the tube and a liposomal solution can be obtained by ultrasonication for 5 minutes in an ice bath using an Ultrasonic Processor (Heat Systems, Inc., Farmingdale, N.Y.).

The spherical or ellipsoid shape, e.g. bead, is preferably also coated with a substance that will help attract and anchor a lipid layer. For example, one can use a compound such as streptavidin or avidin to coat the spherical or ellipsoid shape such as a bead and add a small amount of biotinylated lipid to the lipid mixture. For example, one can use a head group-modified synthetic lipid, such as dipalmitoylphosphoethanolamine-N-Biotinyl (Biotinyl-DPPE) or dioleoylphosphoethanolamine-lissamine Rhodamine B (Rho-DOPE) in solution with lipids. Such a mixture will form a strong uniform coating with, for example, a streptavidin coated-bead. Liposomal solutions of the head group-modified synthetic lipids 1,2-dioleyl-sn-glycero-3-phosphoethanolamine-n-(biotinyl) (Biotinyl-DOPE) and dioleoylphosphoethanolamine-lissamine rhodamine B (Rho-DOPE), at a final concentration of 1 mg/ml, can be prepared separately using the same protocol as described above for the non-labeled lipid solutions.

The spherical or ellipsoid shape (such as a bead) will also have an anchor ligand such as an antibody bound to it that will specifically bind either the antigenic tag or a known specific portion of the integral membrane protein that is to be bound to the bead, thereby orienting the protein. The lipid solution containing biotinylated lipid is added to the beads with the captured protein of interest. Thereafter, the detergent is slowly removed by known means. For example, by dialysis, for e.g., at least 24 hours. The resulting integral membrane protein-containing proteoliposome is stable for an extended period of time. As used herein, an extended period of time means at least 12 hours; still more preferably at least one day; even more preferably at least one week; still more preferably at least one month; and even more preferably at least two months. Not only will the protein retain its conformation in these proteoliposomes for long periods of time, but it will do so under a wide range of conditions, such as pH and temperature.

Preferably the spherical or elliptoid surface that is used is a magnetic bead. Magnetic beads are well known in the art and can be obtained commercially. For example tosylactivated Dynabeads® M-(Bikker, J. A., Trumpp-Kallmeyer, S., and Humblet, C. (1998) J. Med. Chem. 41, 2911-2927)0 (Dynal, Inc., Lake Success, N.Y.). These are particularly useful in assisting in the purification of the protein. One can use such proteoliposomes as intermediates and transfer the stabilized proteoliposome to another surface. For example, a flake. When using the proteoliposome for injection into an individual, it is preferable that the surface is made of a biodegradable material.

While the proteoliposome will typically contain only the integral membrane protein of interest, there are instances where one may want to use more than one protein. For example, the chemokine receptor CCR5 is known to cooperate with the single transmembrane-spanning protein, CD4, in interacting with the HIV gp120 protein. Thus, one can prepare proteoliposomes containing CD4 as well as the envelope glycoprotein. In another embodiment one can have both CCR5 and CD4 as well as the envelope glycoprotein. This can readily be done by tagging the proteins with the same epitope tag at the C-terminus and preparing beads with the appropriate tag-reactive antibody. Alternatively, the proteins can be tagged with different tags and one can prepare beads having mixtures of different antibodies. This would allow one to vary the ratios of the two proteins in the proteoliposome.

These stabilized proteoliposomes can be used in a variety of different methods.

One can obtain high concentrations of the protein on the bead. In this manner one can use the proteoliposome as an immunogen to obtain antibodies to the native confirmation of the protein. One can use the proteoliposomes to obtain antibodies to different epitopes exposed during different conformations of a protein. For example, one protein may assemble into several different multimeric complexes, depending for example on the availability of different binding partners. Proteoliposomes carrying different complexes can be used as immunogens, thus generating antibodies to different epitopes on a single protein which are differentially exposed depending on its binding to other proteins.

The immunogenic proteoliposomes can be used to generate and also to identify a range of antibodies. For example, antibodies to gp120 and gp41 (or gp135 and gp35). For example, antibodies that affect the interaction with the receptor binding sites can be directly screened for, for instance by using a direct binding assay. For example, one can use a radioactive or fluorescent marker to label the gp120 proteoliposome and add soluble CD4, or more preferably a proteoliposome containing CD4. There are various soluble CD4s known in the art including a two-domain (D1D2 sCD4) and a four-domain version. The CD4 proteoliposomes can be added to medium containing the gp120 proteoliposome and an antibody that will block binding between the two proteoliposomes can be screened for. In another example, the proteoliposome can contain both gp120 and CD4 and you can look at interactions with CCR5. Alternatively, when using a derivative from a T cell tropic gp120 one would use a proteoliposome containing CXCR4. Binding can then be directly measured. The antibody of interest can be added before or after the addition of the labeled proteoliposome and the effect of the antibody on binding can be determined by comparing the degree of binding in that situation against a base line standard with that proteoliposome, in the absence of the antibody.

A preferred assay uses the labeled proteoliposome, for example containing a gp120 trimer derived from an M-tropic strain such as JR-FL, iodinated using for instance solid phase lactoperoxidase (in one example having a specific activity of 20 $\mu$Ci/$\mu$g). The proteoliposome containing the chemokine receptor in this example would contain CCR5. Soluble CD4 could be present.

gp120 Derivatives

The proteoliposome can contain a variety of envelope glycoprotein derivatives.

In one embodiment, the envelope glycoprotein trimer is composed of variable region-deleted gp120 or gp125 such as described in U.S. Pat. Nos. 5,858,366 and 5,817,316. For example, the conformational gp120 portion should contain a sufficient number of amino acid residues to define the binding site of the gp120 to the chemokine receptor (e.g. sequences from the fourth conserved region and from the V3 loop) and a sufficient number of amino acids to maintain the conformation of the peptide in a conformation that approximates that of wild-type gp120 bound to soluble CD4 with respect to the chemokine receptor binding site. In other embodiments the V3 loop can be removed to remove masking amino acid residues. In order to maintain the conformation of the polypeptide one can insert linker residues that permit potential turns in the polypeptides structure. For example, amino acid residues such as Gly, Pro and Ala. Gly is preferred. Preferably, the linker residue is as small as necessary to maintain the overall configuration. It should typically be smaller than the number of amino acids in the variable region being deleted. Preferably, the linker is 8 amino acid residues or less, more preferably 7 amino acid residues or less. Even more preferably, the linker sequence is 4 amino acid residues or less. In one preferred embodiment the linker sequence is one residue. Preferably, the linker residue is Gly.

In one preferred embodiment, the gp120 portion also contains a CD4 binding site (e.g. from the C3 region residues 368 and 370, and from the C4 region residues 427 and 457). The chemokine binding site is a discontinuous binding site that includes portions of the C2, C3, C4 and V3 regions. By deletion of non-essential portions of the gp120 polypeptide—such as deletions of portions of non-essential variable regions (e.g. V1/V2) or portions in the constant regions (e.g. C1, C5) one can increase exposure of the CD4 binding site. Another embodiment is directed to a gp120 portion containing a chemokine binding site. Similarly, by deleting the non-essential portions of the protein one can increase exposure of the chemokine binding site. The increased exposure enhances the ability to generate an antibody to the CD4 receptor or chemokine receptor, thereby inhibiting viral entry. Removal of these regions is done while requiring the derivative to retain an overall conformation approximating that of the wild-type protein with respect to the native gp120 binding region, e.g. the chemokine binding region when complexed to CD4. In addition, one can remove glycosylation sites that are dispensable for proper folding. Maintaining conformation can be accomplished by using the above-described linker residues that permit potential turns in the structure of the gp120 derivative to maintain the overall three-dimensional structure. Preferred amino acid residues that can be used as linker include Gly and Pro. Other amino acids can also be used as part of the linker, e.g. Ala. Examples on how to prepare such peptides are described more fully in Wyatt, R., et al., *J. Virol.* 69: 5723-5733, 1995; Thali, M., et al., *J. Virol.* 67: 3978-3988, 1993; and U.S. Pat. Nos. 5,858,366 and 5,817,316, which are incorporated herein by reference.

An alternative gp120 derivative is one wherein the linkers used result in a conformation for the derivative so that the discontinuous binding site with the chemokine receptor approximates the conformation of the discontinuous binding site for the chemokine receptor in the wild-type gp120/CD4 complex. These derivatives can readily be made by the person of ordinary skill in the art based upon the above described methodologies and screened in the assays shown herein to ensure that proper binding is obtained.

In one embodiment, at least one sugar addition site is deleted. Preferably the sugar addition site is near a conformational epitope. This can be accomplished by known means. For example, the amino acid can be deleted. In one embodiment that deleted amino acid can be replaced by another residue that will not form a sugar addition site.

In a preferred embodiment, multiple sugar addition sites can be deleted. In a still more preferred embodiment the sugar addition sites can be deleted from the variable loop deleted monomers.

Generating Antibodies

These immunogenic proteoliposomes can be used to generate an immune reaction in a host by standard means. For example one can administer the proteoliposome in adjuvant.

The proteoliposome is preferably administered with an adjuvant. Adjuvants are well known in the art and include aluminum hydroxide, Ribi adjuvant, etc. Preferably the proteoliposome is comprised of biodegradable material.

One can administer these proteoliposomes to individuals by a variety of means. For immunization purposes, intradermal, subcutaneous, intramuscular and mucosal administration can be used.

The proteoliposomes when used for administration are prepared under aseptic conditions with a pharmaceutically acceptable carrier or diluent.

Doses of the pharmaceutical compositions will vary depending upon the subject and upon the particular route of administration used. Dosages can range from 0.1 to 100,000 µg/kg a day, more preferably 1 to 10,000 µg/kg.

Routes of administration include oral, parenteral, rectal, intravaginal, topical, nasal, direct injection, etc.

An exemplary pharmaceutical composition is a therapeutically effective amount of an oligomer, antibody etc., that for example affects the ability of the receptor to facilitate HIV infection, or that can induce an immune reaction, thereby acting as a prophylactic immunogen, optionally included in a pharmaceutically-acceptable and compatible carrier. The term "pharmaceutically-acceptable and compatible carrier" as used herein, and described more fully below, includes one or more compatible solid or liquid filler diluents or encapsulating substances that are suitable for administration to a human or other animal. In the present invention, the term "carrier" thus denotes an organic or inorganic ingredient, natural or synthetic, with which the molecules of the invention are combined to facilitate application. The term "therapeutically-effective amount" is that amount of the present pharmaceutical composition which produces a desired result or exerts a desired influence on the particular condition being treated. For example, the amount necessary to raise an immune reaction to provide prophylactic protection. Typically when the composition is being used as a prophylactic immunogen at least one "boost" will be administered at a periodic interval after the initial administration. Various concentrations may be used in preparing compositions incorporating the same ingredient to provide for variations in the age of the patient to be treated, the severity of the condition, the duration of the treatment and the mode of administration.

In one preferred method of immunization one would prime with a proteoliposome containing variable loop deleted gp120 trimer, and then boost with a proteoliposome containing a gp120 trimer that more closely approximates the wild type viral glycoprotein until at least one final boost with proteoliposomes containing the stabilized wild type trimer. For example, if multiple variable regions and sugar addition sites are deleted from the priming trimer, the next boost will be with a trimer where more variable region amino acids are present and/or sugar addition sites present. Each boost will get closer to the wild type configuration until that configuration is reached.

Doses of the pharmaceutical compositions of the invention will vary depending on the subject and upon the particular route of administration used. Dosages can range from 0.1 to 100,000 µg/kg per day, more preferably 1 to 10,000 µg/kg. By way of an example only, an overall dose range of from about, for example, 1 microgram to about 300 micrograms might be used for human use. This dose can be delivered at periodic intervals based upon the composition. For example on at least two separate occasions, preferably spaced apart by about 4 weeks. In the embodiment where the prime is the proteoliposome containing the variable loop deleted gp120 trimers, with the boost of proteoliposomes containing native gp120, or native gp120, it is presently preferred to have a series of at least 2 boosts, preferably 3 to 5 boosts spread out over a year. Other compounds might be administered daily. Pharmaceutical compositions of the present invention can also be administered to a subject according to a variety of other, well-characterized protocols. For example, certain currently accepted immunization regimens can include the following: (i) administration times are a first dose at elected date; a second dose at 1 month after first dose; and a third dose at a subsequent date, e.g., 5 months after second dose. See Product Information, *Physician's Desk Reference*, Merck Sharp & Dohme (1990), at 1442-43. (e.g., Hepatitis B Vaccine-type protocol); (ii) for example with other vaccines the recommended administration for children is first dose at elected date (at age 6 weeks old or older); a second dose at 4-8 weeks after first dose; a third dose at 4-8 weeks after second dose; a fourth dose at 6-12 months after third dose; a fifth dose at age 4-6 years old; and additional boosters every 10 years after last dose. See Product Information, *Physician's Desk Reference*, Merck Sharp & Dohme (1990), at 879 (e.g., Diphtheria, Tetanus and Pertussis-type vaccine protocols). Desired time intervals for delivery of multiple doses of a particular composition can be determined by one of ordinary skill in the art employing no more than routine experimentation.

Antibodies

The term "antibodies" is meant to include monoclonal antibodies, polyclonal antibodies and antibodies prepared by recombinant nucleic acid techniques that are selectively reactive with polypeptides encoded by nucleotide sequences of the present invention. The term "selectively reactive" refers to those antibodies that react with one or more antigenic determinants on e.g. gp120 and do not react with other polypeptides. Antigenic determinants usually consist of chemically active surface groupings of molecules such as amino acids or sugar side chains and have specific three dimensional structural characteristics as well as specific charge characteristics. Antibodies can be used for diagnostic applications or for research purposes, as well as to block binding interactions.

For preparation of antibodies directed toward the immunogenic proteoliposomes, any technique that provides for the production of antibody molecules may be used.

For example, mice can be immunized twice intraperitoneally with approximately 50 micrograms of proteoliposome immunogen per mouse. Sera from such immunized mice can be tested for antibody activity by immunohistology or immunocytology on any host system expressing such polypeptide or against another proteoliposome or by ELISA with the expressed polypeptide. For immunohistology, active antibodies of the present invention can be identified using a biotin-conjugated anti-mouse immunoglobulin followed by avidin-peroxidase and a chromogenic peroxidase substrate. Preparations of such reagents are commercially available; for example, from Zymed Corp., San Francisco, Calif. Mice whose sera contain detectable active antibodies according to the invention can be sacrificed three days later and their spleens removed for fusion and hybridoma production. Positive supernatants of such hybridomas can be identified using the assays described above and by, for example, Western blot analysis.

Another method for preparing antibodies is by using hybridoma mRNA or splenic mRNA as a template for PCT amplification of such genes [Huse, et al., *Science* 246:1276 (1989)]. For example, antibodies can be derived from murine monoclonal hybridomas [Richardson, J. H., et al., *Biochem and Biophys Res Comm.* 197: 422-427 (1993); Mhashilkar, A. M., et al., *EMBO J.* 14:1542-1551 (1995)]. These hybridomas provide a reliable source of well-characterized reagents for the construction of antibodies and are particularly useful when their epitope reactivity and affinity has been previously characterized. Another source for such construction includes the use of human monoclonal antibody producing cell lines [Marasco, W. A., et al., *Proc. Natl. Acad. Sci. USA* 90:7889-7893 (1993); Chen, S. Y., et al., *Proc. Natl. Acad. Sci. USA* 91:5932-5936 (1994)]. Another example includes the use of antibody libraries such as phage display technology to construct new antibodies against different epitopes on a target molecule [Burton, D. R., et al., *Proc. Natl. Acad. Sci. USA* 88:10134-1-137 (1991); Hoogenboom, H. R., et al., *Immunol. Rev.* 130:41-68 (1992); Winter, G., et al., *Ann. Rec. Immunol.* 12:433-355 (1994); Marks, J. D., et al., *J. Biol. Chem.* 267:16007-16010 (1992); Nissim, A., et al., *EMBO J.* 13:692-698 (1994); Vaughan, T. J., et al., *Nature Bio.* 14:309-314 (1996); Marks, C., et al., *New Eng. J. Med.* 335: 730-733 (1996)]. For example, very large naïve human sFV libraries have been and can be created to offer a large source of rearranged antibody genes against a plethora of target molecules. Smaller libraries can be constructed from individuals with autoimmune disorders [Portolano, S., et al., *J. Immunol.* 151: 2839-2851 (1993); Barbas, S. M., et al., *Proc. Natl. Acad. Sci. USA* 92:2529-2533 (1995)] or infectious diseases [Barbas, C. F., et al., *Proc. Natl. Acad. Sci. USA* 89:9339-9343 (1992); Zebedee, S. L., et al., *Proc. Natl. Acad. Sci. USA* 89:3175-3179 (1992)] in order to isolate disease specific antibodies. Thereafter one can use these proteoliposomes to screen such libraries to identify the desired antibodies.

Other sources include transgenic mice that contain a human immunoglobulin locus instead of the corresponding mouse locus as well as stable hybridomas that secrete human antigen-specific antibodies [Lonberg, N., et al., *Nature* 368: 856-859 (1994); Green, L. L., et al., *Nat. Genet.* 7:13-21 (1994)]. Such transgenic animals provide another source of human antibody genes through either conventional hybridoma technology or in combination with phage display technology. In vitro procedures to manipulate the affinity and find specificity of the antigen binding site have been reported including repertoire cloning [Clackson, T., et al., *Nature* 352: 624-628); marks, J. D., et al., *J. Mol. Biol.* 222: 581-597 (1991); Griffiths, A. D., et al., *EMBO J.* 12: 725-734 (1993)], in vitro affinity maturation [Marks, J. D., et al., *Biotech* 10: 779-783 (1992); Gram, H., et al., *Proc. Natl. Acad. Sci. USA* 89: 3576-3580 (1992)], semi-synthetic libraries [Hoogenboom, H. R., supra; Barbas, C. F., supra; Akamatsu, Y., et al., *J. Immunol.* 151: 4631-4659 (1993)] and guided selection [Jespers, L. S. et al., *Bio Tech* 12: 899-902 (1994)]. Starting materials for these recombinant DNA based strategies include RNA from mouse spleens [Clackson, t., supra] and human peripheral blood lymphocytes [Portolano, S., et al., supra; Barbas, C. F., et al., supra; Marks, J. D., et al., supra; Barbas, C. F., et al., *Proc. Nat. Acad. Sci. USA* 88: 7978-7982 (1991)] and lymphoid organs and bone marrow from HIV-1-infected donors [Burton, D. R., et al., supra; Barbas, C. F., et al., *Proc. Natl. Acad. Sci. USA* 89:9339-9343 (1992)].

For preparation of monoclonal antibodies directed toward the immunogenic proteoliposomes, any technique that provides for the production of antibody molecules by continuous cell lines may be used. For example, the hybridoma technique originally developed by Kohler and Milstein (*Nature,* 256: 495-7, 1973), as well as the trioma technique, the human B-cell hybridoma technique (Kozbor et al., *Immunology Today* 4:72), and the EBV-hybridoma technique to produce human monoclonal antibodies, and the like, are within the scope of the present invention. See, generally Larrick et al., U.S. Pat. No. 5,001,065 and references cited therein. Further, single-chain antibody (SCA) methods are also available to produce antibodies against polypeptides encoded by a eukaryotic nucleotide sequence of the invention (Ladner et al., U.S. Pat. Nos. 4,704,694 and 4,976,778).

Murine monoclonal antibodies can be "humanized" by known techniques.

The monoclonal antibodies may be human monoclonal antibodies or chimeric human-mouse (or other species) monoclonal antibodies. The present invention provides for antibody molecules as well as fragments of such antibody molecules.

Those of ordinary skill in the art will recognize that a large variety of possible moieties can be coupled to the resultant antibodies or preferably to the stabilized trimers or to other molecules of the invention. See, for example, "Conjugate Vaccines", *Contributions to Microbiology and Immunology*, J. M. Cruse and R. E. Lewis, Jr (eds.), Carger Press, New York, 1989, the entire contents of which are incorporated herein by reference.

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, disocyanates, glutaraldehydes, diazobenzenes and hexamethylene diamines. This listing is not intended to be exhaustive of the various classes of coupling agents known in the art but, rather, is exemplary of the more common coupling agents (see Killen and Lindstrom, *J. Immunol.* 133:1335-2549, 1984; Jansen, F. K., et al., *Imm. Rev.* 62:185-216, 1982; and Vitetta et al., supra).

Preferred linkers are described in the literature. See, for example, Ramakrishnan, S., et al., *Cancer Res.* 44: 201-208 (1984), describing the use of MBS (M-maleimidobenzoyl-N- hydroxysuccinimide ester). See also Umemoto et al., U.S. Pat. No. 5,030,719, describing the use of a halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6 [3-(2-pyridyldithio) propionamido] hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Complexes that form with molecules of the present invention can be detected by appropriate assays, such as the direct binding assay discussed earlier and by other conventional types of immunoassays.

In a preferred embodiment, one could screen a phage display library looking to find antibodies to a given protein or find ligands that will bind to the protein.

One can also use these proteoliposomes to screen libraries for a desired compound. One can also use these proteoliposomes to screen complex chemical libraries of small molecular weight (<1000 daltons) compounds to identify high-affinity ligands. These compounds could serve as lead compounds for the discovery of agonistic and antagonistic drugs.

If one knows a ligand that interacts with the protein, one can use these proteoliposomes in assays to screen for compounds that modulate such interactions with the protein. For example, in the aforementioned CCR5/CD4-containing proteoliposomes, one can add the oligomeric gp120 or oligomeric gp160 to the mixture and add other compounds to see their effect on the formation or stability of the CD4/gp120/CCR5 complex.

One can also use the antibody tag to reverse-orient the proteoliposome. As used herein a reverse-oriented protein will have the portion of the protein that is normally present intracellularly present on the surface of the proteoliposome. Then one can screen for compounds or proteins that affect intracellular interactions. For example, one can look at the binding of intracellular as well as extracellular ligands, as well as compounds or proteins that will affect intracellular as well as extracellular binding.

One can also use this method to identify small antagonists in an assay that looks at compounds that affect binding of a known ligand. For instance, the entry of human immunodeficiency virus (HIV-1) into host cells typically requires the sequential interaction of the gp120 exterior envelope glycoprotein with the CD4 glycoprotein and a chemokine receptor on the cell membrane. CD4 binding induces conformational changes in gp120 that allow high-affinity binding to the chemokine receptor. The chemokine receptor CCR5 is the principal HIV-1 coreceptor used during natural infection and transmission. Individuals with homozygous defects in CCR5 are healthy but relatively resistant to HIV-1 infection. Although some HIV-1 isolates can be adapted in tissue culture to replicate on cells lacking CD4, binding to the chemokine receptor appears to be essential for virus entry into the host cell. These observations suggest that inhibiting the gp120-CCR5 interaction might be a useful therapeutic or prophylactic approach to HIV-1 infection. A chemokine analogue, AOP-RANTES (Simmons, G. et al. (1997), *Science:* 276: 276-279), and a small molecular weight compound (TaKeda) (Baba, M. et al. (1999), *Proc. Natl. Acad. Sci. USA* 96: 5698-5703) have been identified that bind CCR5 and inhibit HIV-1 infection in tissue culture, although clinical utility remains to be demonstrated.

When solubilized using specific detergent and salt conditions, human CCR5 can retain its ability to bind HIV-1 gp120-CD4 complexes and conformation-dependent monoclonal antibodies (Mirzabekov et al., JBC). However, the detergent-solubilized CCR5 exhibits very stringent requirements with respect to the conditions under which native conformation is retained and has limited longevity. Thus, it is impractical to use purified preparations of solubilized CCR5 in screening assays. CCR5-proteoliposomes have homogeneous, native CCR5 affixed to the surface of a paramagnetic bead in an oriented manner. The preparation of CCR5-proteoliposomes is relatively independent of the CCR5 density on the surface of the cells used as a source of the chemokine receptor, and also allows the concentration of CCR5 on the bead surface. A lipid bilayer, such as that reconstituted around the bead, provides a natural membrane environment for the CCR5 protein, allowing long-term maintenance of the native CCR5 conformation.

Accordingly, the present method creates an easily manipulable spherical lipid bilayer containing a relatively large amount of pure, oriented and stable integral membrane protein. This permits these proteins to be used in applications that have previously been restricted to the use of soluble purified proteins.

As a specific example, paramagnetic, nonporous beads surrounded by a lipid membrane bilayer containing human gp120-CCR5 mixtures in a native conformation can be prepared as set forth below. Human CCR5 can be expressed in Cf2Th canine thymocytes transfected with a codon-optimized CCR5 gene. The CCR5 protein contains a C-terminal nonapeptide (C9) tag that is recognized by the 1D4 monoclonal antibody. In a first approach, lysates from CCR5-expressing Cf2Th cells (Cf2Th-CCR5) were prepared using the detergents shown to allow retention of native CCR5 formation. CCR5 was affinity-purified from the lysates using 1D4-Sepharose beads and eluted using the C9 nonapeptide corresponding to the C-terminal epitope tag.

Paramagnetic beads were conjugated with both the 1D4 antibody and the streptavidin. The 1D4 antibody allowed simple purification and concentration of CCR5 from cell lysates, as well as its orientation on the bead surface. The streptavidin allowed stable and saturating membrane reconstitution around the bead. A 10:1 molar ratio of 1D4 antibody: streptavidin was found to be optimal with respect to the highest density of reconstituted CCR5 and the completeness of the membrane in the paramagnetic proteoliposomes (data not shown). It is possible to vary the antibody:streptavidin ratio, if necessary, from 100:1 to 1:1000 or less in different applications.

CCR5-proteoliposomes prepared by this approach exhibited the most efficient recognition by the 2D7 conformation-dependent antibody. In fact, recognition by the 2D7 antibody was practically equal to that of the 5C7 antibody (data not shown), indicating that the vast majority of CCR5 in these proteoliposomes preparations is in a native conformation. The envelope glycoprotein can be combined on the proteoliposome as discussed above.

The paramagnetic proteoliposomes are stable for extended periods of time. The integrity of the conformational dependent epitope on the proteins such as the gp120 proteins is maintained for extended periods of time permitting the uses described above.

EXAMPLES

Example 1

Conformational Characterization of Proteoliposomes Containing gp160

Envelope Glycoprotein Constructs

The envelope glycoprotein constructs were derived from the primary R5 HIV-1 isolates YU2 and JR-FL and the X4, TCLA-adapted isolate HXBc2. The coding sequences for the YU2 envelope glycoprotein were obtained from the pSVII-IenvYU2 expression plasmid. The JR-FL envelope glycoprotein coding sequence, which contains a CD5 heterologous leader sequence in place of the normal JR-FL leader, was obtained from the AIDS repository and subcloned into the pcDNA 3.1(−) (Invitrogen) expression plasmid. The HXBc2 construct was codon-optimized for mammalian expression using overlapping primers and PCR and subcloned into pcDNA3.1(+) (Invitrogen). A sequence coding for the heterologous CD5 signal sequence was subcloned to replace the endogenous HXBc2 leader sequence. To all constructs, the cytoplasmic tail truncation was generated by introduction of a stop codon in place of the codon for amino acid 712 and the sequence coding for the C9-tag TETSQVAPA was added according to the QuikChange protocol immediately before the stop codon. To create covalently linked gp120-gp41 glycoproteins, the proteolytic cleavage site between gp120 and gp41 was disrupted by replacing the arginines 508 and 511 with serines by QuikChange site-directed mutagensis. These modifications resulted in constructs encoding cleavage-deficient gp160ΔCT envelope glycoproteins used to generate the proteoliposomes. Amino acid residue numbers are designated according to the prototypic HXBc2 sequence. The constructs were sequenced and introduction of the desired mutations was confirmed by this method.

Envelope Glycoprotein Expression

Plasmids expressing the gp160ΔCT glycoproteins (2 μg DNA per 100 mm dish of cells) were cotransfected into 293T cells with (YU2) or without (JR-FL, HXBc2) the HIV-1 Tat expressor plasmid pSVTat (0.5 μg), using Effectene reagent (QIAGEN) following the manufacturer's protocol. Thirty-six hours after transfection, cells expressing the envelope glycoproteins were harvested with PBS containing 5 mM EDTA.

Coating of Dynabeads M-450

Tosyl-activated Dynabeads (Dynal, Inc., Lake Success, N.Y.) were conjugated with the 1D4 antibody (National Cell Culture Center, Minneapolis, Minn.) according to the manufacture's protocol. The 1D4 murine antibody recognizes the C9 epitope tag and was used to capture the envelope glycoproteins on the Dynal beads.

Preparation of Lipid Solutions for Membrane Reconstitution

Lipids were obtained as chloroform solutions from Avanti Polar Lipids (Alabaster, Ala.). The following lipids were used: 1-Palmitoyl-2-Oleoyl-sn-Glycero-3-Phosphocholine (POPC), 1-Palmitoyl-2-Oleoyl-sn-Glycero-3-Phosphoethanolamine (POPE) and Dimyristoylphosphatidic acid (DMPA) and Cholesterol at molar concentrations 45:25:20:10. The lipid mixture was dried in a 2-ml polyethylene tube under a vacuum until all of the solvent was removed. PBS was added to the tube and a liposomal solution was obtained by ultrasonication for 5 minutes in an ice bath using an Ultrasonic Processor (Heat Systems, Inc., Farmingdale, N.Y.). Liposomal solutions of the head group-modified synthetic lipids 1,2-dioleyl-sn-glycero-3-phosphoethanolamine-n-(biotinyl) (Biotinyl-DOPE) and dioleoylphosphoethanolamine-lissamine rhodamine B (Rho-DOPE), at a final concentration of 1 mg/ml, were prepared separately using the same protocol.

Formation of Proteoliposomes

For the preparation of $4 \times 10^8$ proteoliposomes, approximately $2 \times 10^7$ gp160ΔCT-expressing 293T cells were lysed in 5 ml solubilization buffer (100 mM $(NH_4)_2SO_4$, 20 mM Tris-HCl (pH 7.5), 1% (w/v) Cymal™-5 and Protease Inhibitor Mixture (one tablet of Complete™ [Boehringer Mannheim] per 50 ml) at 4° C. for 30 minutes on a rocking platform. Cell debris was pelleted by centrifugation for 30 minutes at 13,000 g. The cleared lysate was incubated with $4 \times 10^8$ 1D4-conjugated Dynal beads for 16 hours at 4° C. on a rocking platform. After recovery of the beads, they were extensively washed in solubilization buffer. For the formation of the lipid membrane, beads coated with gp160ΔCT glycoprotein were incubated for 15 minutes at RT with 1 ml solubilization buffer containing 2 mg of lipid mixture, and, if fluorescence labeling or biotinylation was desired, with 1% of Rho-DOPE or biotin-PE. The detergent was then slowly removed by dialysis for 24 hours at 4° C. against PBS, using a 10 kDa molecular weight cutoff dialysis membrane (Slide-A-Lyzer® 10 K [Pierce, Rockford, Ill.]). The excess of unbound lipid and residual detergent was removed on a magnetic separator in one washing step with PBS. Proteoliposomes were stored in PBS with 0.1% BSA and 0.1% $Na_2N_3$ at 4° C. for up to three months.

Analysis of Protein Composition of the Proteoliposomes

Figure 2:
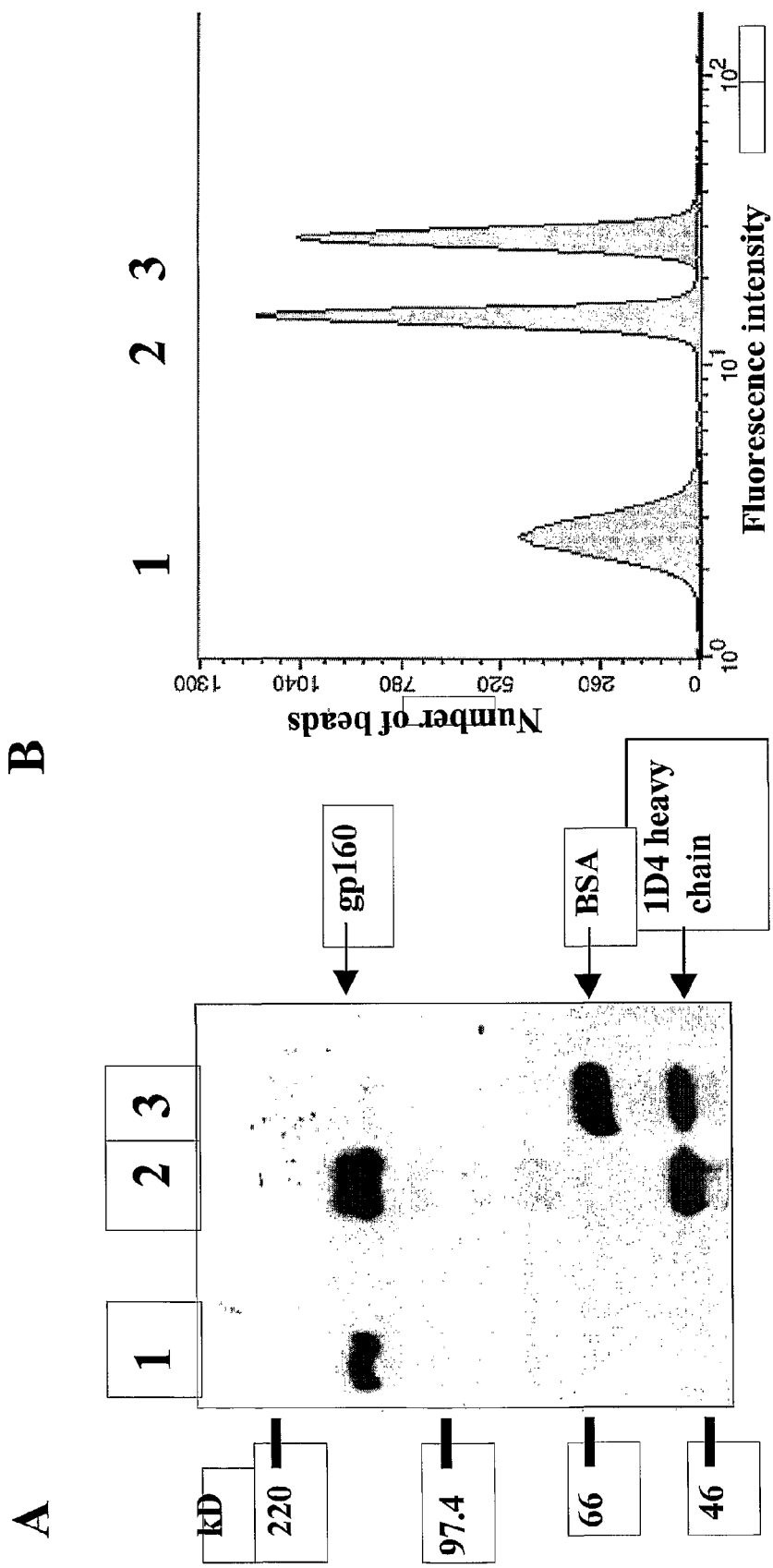
FIGS. 2A-B show protein composition of PLs.

Approximately $5 \times 10^7$ PLs and control beads were incubated at 100° C. in reducing SDS-sample buffer for 5 minutes, separated on a 7.5% SDS-polyacrylamide gel and stained with Coomassie blue. For the analysis of fractions eluted by molecular exclusion, Western blotting was performed under either non-reducing or reducing conditions. To determine that gp120 was present in the eluted protein peaks, samples from each peak were incubated for 5 minutes at 100° C. in sample buffer containing 2% BME and separated on a 7.5% SDS-polyacrylamide gel (FIG. 2B). To confirm that oligomeric forms of envelope glycoproteins could be detected in the high molecular weight peaks, the fractions were diluted in sample buffer lacking BME and separated on a 3-8% SDS-polyacrylamide gel. A sample from the peak consistent with a trimer (fraction 3, FIG. 4) was also analyzed in the presence of BME. Subsequently, proteins were electrophoretically transferred onto a 0.45 μm Hybond-C extra membrane (Amersham). The gp160ΔCT glycoproteins present in each column fraction were then detected by anti-gp120 rabbit serum and anti-rabbit IgG-horseradish peroxidase (HRP) (Sigma).

Molecular Exclusion Chromatography

The gp160ΔCT glycoproteins captured onto Dynal beads were eluted from the beads for molecular exclusion chromatography under non-denaturing conditions as follows. The beads were incubated in 0.5 M $MgCl_2$, 1% CHAPS, and 0.2 mM C9 peptide (peptide sequence: TETSQVAPA) at 37° C. for 30 minutes. Approximately 5 µg of eluted gp160ΔCT glycoproteins were loaded onto a Superdex 200 column (Amersham Pharmacia Biotech) in a 200 µl volume. The column was then eluted with PBS containing 1% CHAPS at a rate of 0.5 ml/min for 40 minutes. The eluted protein was detected by measuring the optical density at 280 nm (OD280) using a Varian ProStar System (Varian Analytical Instruments). Fractions of the flow-through were collected at 2 minute intervals using a Varian Dynamax Fraction Collector. The fractions were further analyzed by reducing and non-reducing SDS-PAGE and Western blotting using a polyclonal anti-gp120 rabbit serum for detection of HIV-1 envelope glycoproteins (FIG. 4B-C). A mixture of high molecular weight protein markers (Amersham Pharmacia Biotech) was eluted under identical conditions to calibrate the column.

Flow Cytometric Analysis of gp160ΔCT on Proteoliposomes and 293T Cells

For the comparison of antibody binding to either cleavage-defective or cleavage-competent gp160ΔCT glycoproteins, 293T cells were transfected with plasmids expressing the two envelope glycoprotein variants. Approximately $10^6$ cells per sample were harvested with PBS containing 5 mM EDTA and washed once in FACS buffer (PBS, 2% FCS, 0.02% $Na_2N_3$). The cells were incubated for 1 hour at RT with the indicated amounts of antibodies in a volume of 100 µl. After two washing steps in FACS buffer, the cells were incubated for 30 min with a R-Phycoerythrin (PE)-conjugated F(ab')2 goat anti-human antibody (Jackson Immuno Research Laboratories, Inc., West Grove, Pa.), washed twice and analyzed with a FACScan flow cytometer and CellQuest software (Beckton Dickinson, San Jose, Calif.). For FACS analysis of PLs, staining was performed as described above. Staining for membrane integrity of the PLs was performed using a PE-conjugated goat anti-mouse IgG (Boehringer Mannheim, Indianapolis, Ind.) or Avidin-FITC (Sigma). The following ligands were used for staining of the envelope glycoproteins: soluble CD4, the potently neutralizing CD4BS antibody IgG1b12 (kindly provided by Dennis Burton), the F105 CD4BS antibody (kindly provided by Marshal Posner), the strain-restricted neutralizing V3 loop antibody 39F, the non-neutralizing C1/C4 antibody A32, the non-neutralizing C1/C5 antibody C11, the CD4-induced 17b antibody (all kindly provided by James Robinson) and the broadly neutralizing gp41 antibody 2F5 (kindly provided by Hermann Katinger).

Creation of gp160ΔCT Proteoliposomes

Paramagnetic proteoliposomes (PLs) containing the HIV-1 envelope glycoprotein were created according to methods established for solubilization and membrane reconstitution of the CCR5 chemokine receptor (Mirzabekov et al., Nat. Biotechnol. 18:649-654 (2000)). Briefly, cells transiently expressing the HIV-1 YU2, JR-FL, or HXBc2 gp160ΔCT glycoproteins, which contain an alteration of the gp120-gp41 cleavage site and deletion of the gp41 cytoplasmic tail, were lysed in buffer containing Cymal-5 detergent. The gp160ΔCT glycoproteins were then captured onto Dynal beads conjugated to the 1D4 antibody, which recognizes a C9 peptide tag affixed to the gp160ΔCT C-terminus. Following addition of membrane lipids and dialysis of the Cymal-5 detergent, an artificial lipid bilayer is formed around the bead surface. Thus, pure, properly oriented HIV-1 envelope glycoproteins, embedded in a natural membrane environment were incorporated into an easily manipulable solid support. A schematic of the gp160 proteoliposomes is shown in FIG. 1.

Analysis of Proteoliposome (PL) Protein Composition

The gp160ΔCT PLs were boiled in sample buffer and analyzed by reducing SDS-PAGE to determine their protein composition. As a positive control, cell lysates containing transiently expressed gp160ΔCT glycoproteins were precipitated with the F105 anti-gp120 antibody and protein A-Sepharose and analysed in parallel. PLs lacking the gp160ΔCT glycoproteins were treated similarly and served as a negative control. As seen in FIG. 2A, a band migrating at a position similar to the gp160ΔCT glycoproteins positive control band was observed among the proteins released from the gp160ΔCT PLs. No such band was observed in this molecular weight range in the gp160ΔCT glycoprotein-deficient PL control sample. Apart from a 50 kD band corresponding to the 1D4 antibody heavy chain, a light chain band not retained on the gel, and the band, only minor impurities were detected in the gp160ΔCT PLs. The total amount of gp160ΔCT glycoproteins captured onto $5 \times 10^7$ proteoliposomes was estimated to be 1-2 µg, as determined by the purified recombinant gp160ΔCT glycoproteins control of known concentration.

To examine the exposure of the HIV-1 envelope glycoproteins on the proteoliposome surface, the gp160ΔCT PLs were stained with the IgG1b12 anti-gp120 antibody and a mixture of sera from HIV-1-infected individuals and analyzed by fluorescent activated cell sorting (FACS). The IgG1b12 antibody recognizes a conformation-dependant gp120 epitope near the CD4 binding site. The forward scatter versus sideward scatter plot showed mostly single PLs. Doubles and other multiples of PLs were generally observed to be less than 20% of the total events (data not shown). A gate was created to analyze only single PLs and was used for all further FACS analyses. The narrow distribution of the fluorescence intensity associated with each FACS peak following antibody staining suggests that the gp160ΔCT PLs have nearly uniform protein content (FIG. 2B).

Characterization of the Size of the gp160ΔCT PL Envelope Glycoproteins

The gp160ΔCT glycoproteins were eluted from the reconstituted PLs under non-denaturing conditions by incubation with 0.2 mM C9 peptide in the presence of 1% CHAPS detergent and 0.5 M NaCl. The eluted envelope glycoproteins were analyzed by size-exclusion chromatography on a Superdex 200 column equilibrated in PBS/1% CHAPS buffer. The chromatogram for the HIV-1 JR-FL gp160ΔCT envelope glycoproteins is shown in FIG. 4A. Parallel studies using the YU2 gp160ΔCT glycoproteins yielded a similar profile (data not shown). The fractions of the resolved JR-FL glycoproteins were collected and analyzed by SDS-PAGE and Western blotting (FIG. 4B).

The column was calibrated with molecular weight standards, allowing the apparent molecular size of the major peak to be approximated as 580 kD. As the gp120 glycoprotein monomer was resolved by size-exclusion chromatography with an apparent molecular weight of 180 kD (data not shown and Yang et al., J. Virol. 74:5716-5725 (2000)), a mass of 580 kD is consistent with that of a trimeric gp160ΔCT envelope glycoprotein complex. The fastest migrating protein peak was detected just after the void volume and apparently consists of gp160ΔCT glycoprotein aggregates as determined by its migration pattern in the column and by the Western blot results (FIG. 4). This aggregate peak has previously been observed in molecular exclusion chromatography of soluble GCN4-stablized gp140 trimers (Yang et al., J. Virol. 74:5716-5725 (2000)). Most of the gp160ΔCT glycoprotein eluted in fractions 3 and 4, with fraction 3 corresponding to the mass of 580 kD. When all of the gel filtration fractions were subjected to non-reducing SDS-PAGE followed by Western blotting, fractions 3 and 4, corresponding to trimeric envelope glycoproteins, were found to separate into trimers, dimers and monomers. The greatest degree of gel-stable trimeric glycoproteins were detected in fraction 3 (FIG. 4C). Most of the glycoproteins migrating with molecular weight corresponding to trimers in this fraction could be nearly totally reduced to a monomeric gp160ΔCT band by treatment with 2% β-mercaptoethanol and boiling, although bands migrating in manner consistent with trimers and dimers could still be observed (FIG. 4C).

Characterization of the Proteoliposome Membrane

The formation of the lipid membrane was examined by FACS analysis and fluorescent microscopy. According to our model, the murine 1D4 capture antibody would be expected to be partially occluded by a reconstituted lipid membrane (see FIG. 1). Thereby, binding of anti-mouse IgG antibody should be impaired on proteoliposomes when compared to beads without a membrane. A more than 3-fold decrease of anti-mouse-PE signal could be observed on PLs containing a reconstituted lipid membrane versus beads without lipid reconstitution (FIG. 5B, peak 1 compared to peak 2), indicating the presence of at least a partial lipid membrane.

Figure 3A:
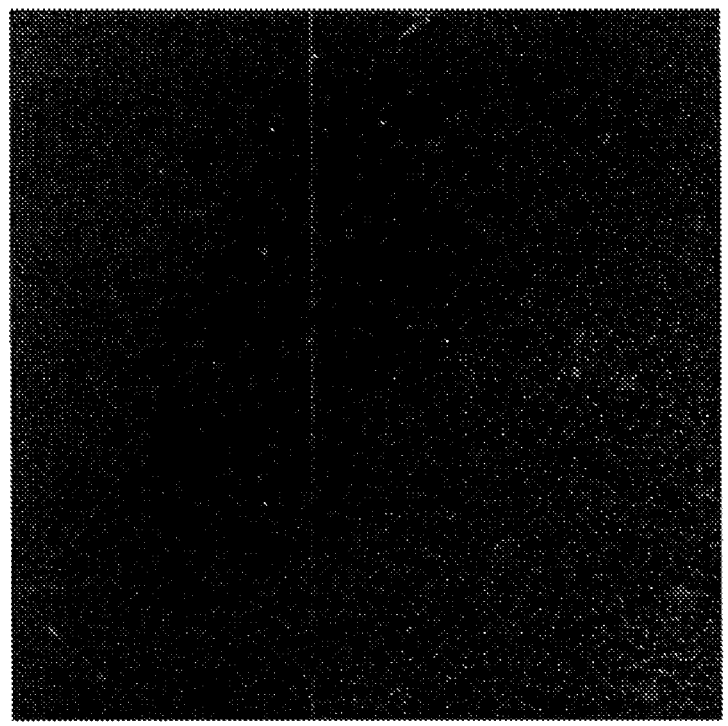
FIGS. 3A-B show fluorescent microscopic pictures of gp160 proteoliposomes.
Figure 3B:
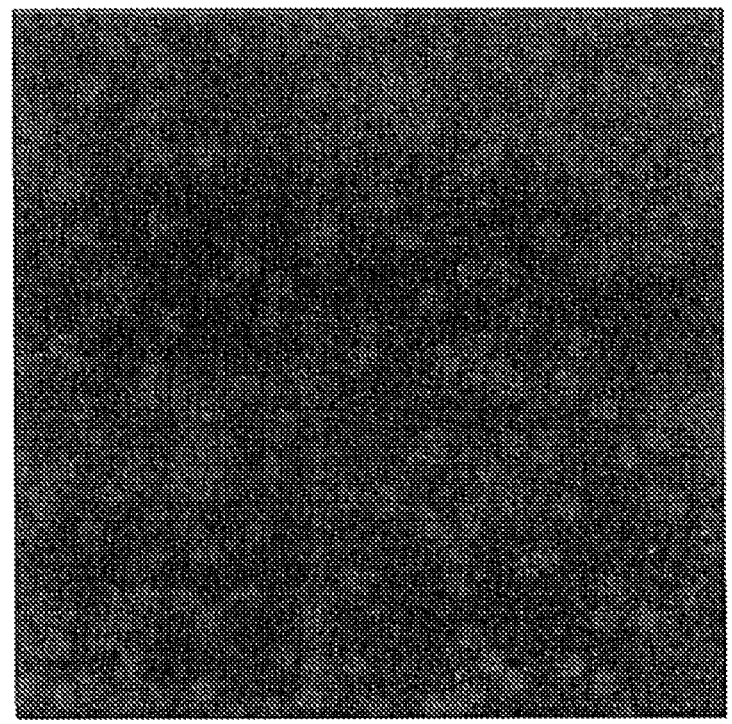
Figure 5:
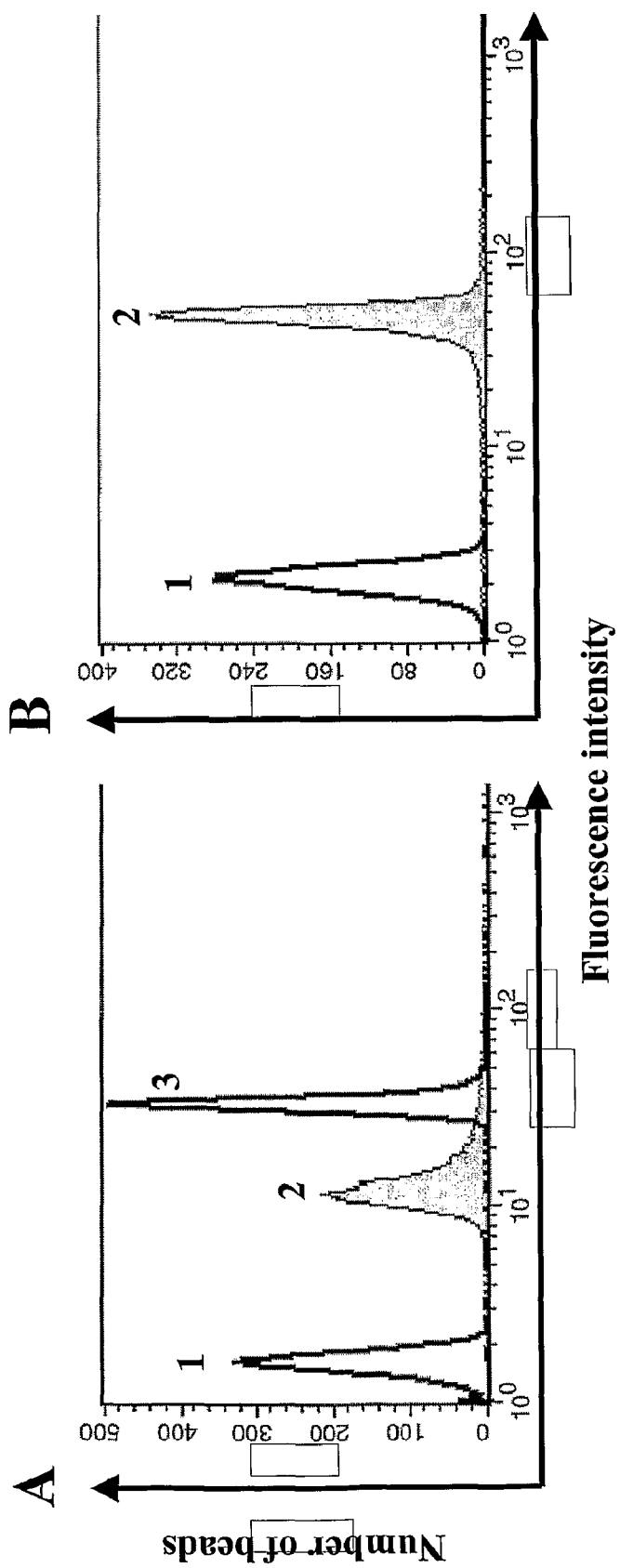
FIG. 5 A-B shows FACS analysis of the reconstituted PL membrane.

The presence of the lipid membrane was also examined by FACS analysis after reconstitution of the membrane with biotinylated lipid at 1% (w/w) of total lipids. The PLs were stained with avidin-FITC and showed more than a 20-fold higher signal on fully reconstituted PLs compared to gp160ΔCT glycoprotein-containing beads without lipid reconstitution (FIG. 5B). We then confirmed the presence of a lipid bilayer by visualizing the incorporation of rhodamine-conjugated lipid (rhodamine-DOPE) into the PL membrane by fluorescent microscopy (FIG. 3). Bright fluorescence could be observed in the rhodamine-labelled PLs (FIG. 3B) compared to negligible background fluorescent emission with untreated beads (FIG. 3A).

2F5 Antibody Binding to gp160ΔCT PLs

Figure 6A:
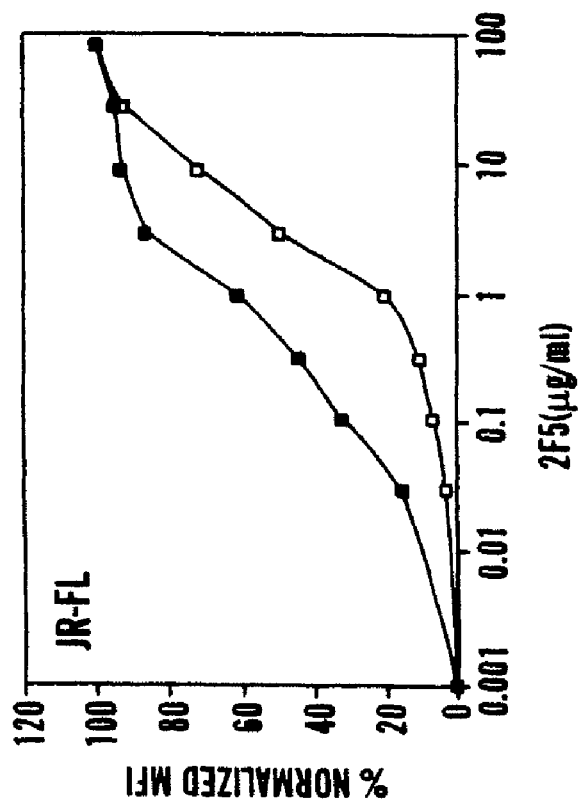
FIG. 6 A-B shows binding of the gp41 antibody 2F5 to gp160ΔCT from HXBc2 (FIG. 6A) and JR-FL (FIG. 6B) on beads without a membrane (open squares) and fully reconstituted PLs (closed squares). PLs and beads, respectively, were probed with increasing concentrations of 2F5 antibody and anti-human IgG PE antibody and analyzed by FACS. The MFI was plotted as % maximal MFI at the given antibody concentration.
Figure 6B:
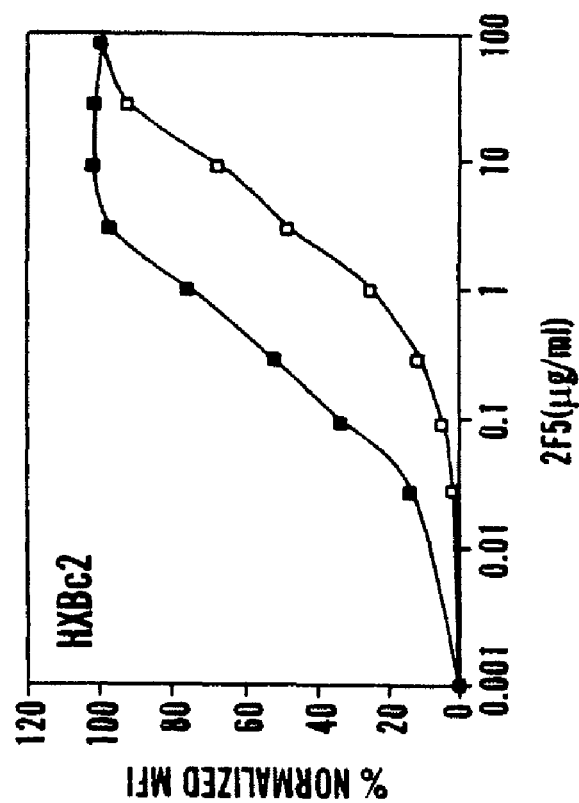

The epitope of the neutralizing antibody 2F5, ELDKWAS, is situated proximal to the viral membrane in the gp41 ectodomain. To determine the influence of the reconstituted membrane on this important neutralizing determinant, we used the 2F5 antibody to probe PLs reconstituted with a membrane and PLs coated with gp160ΔCT glycoprotein but devoid of a membrane. Since sequence variation in the HIV-1 YU2 strain alters 2F5 antibody recognition, PLs with gp160ΔCT glycoproteins derived from the primary isolate JR-FL and the T-Cell line adapted isolate HXBc2 were examined. The 2F5 antibody bound to HXBc2 gp160ΔCT glycoprotein PLs with a reconstituted membrane with roughly a tenfold higher affinity than it did to HXBc2 gp160ΔCT glycoprotein on beads without a membrane. The same could be observed with JR-FL PLs, although the effect was less pronounced (FIG. 6). To rule out unspecific antibody binding effects caused by the presence of the membrane, binding of the gp120-specific F105 antibody to PLs with and without a membrane was examined. No affinity difference could be detected using the F105 antibody (data not shown).

Antigenic Characterization of the gp160ΔCT PLs

Figure 7:
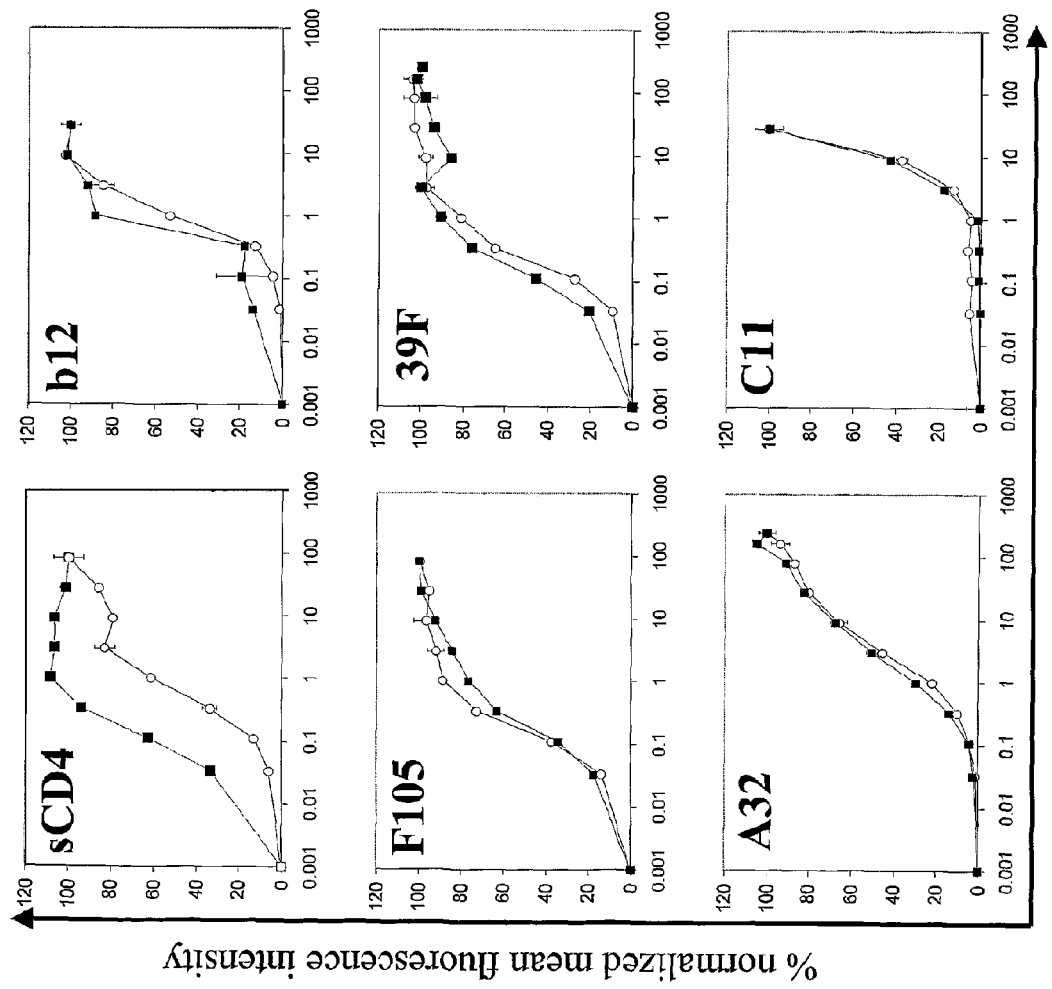
FIG. 7 shows binding of a panel of anti-gp120 antibodies and sCD4 to YU2 gp160ΔCT glycoprotein expressed on 293T cells compared to YU2 gp160ΔCT glycoprotein on PLs. Cells (open circles) and PLs (closed squares) were incubated with increasing amounts of the indicated human antibodies, followed by detection with anti-human IgG PE antibody. For detection of sCD4 binding to the glycoproteins, the rabbit anti-CD4 antibody T45 and anti-rabbit IgG FITC were used. Following staining, samples were analyzed by FACS. The binding of ligands to gp160ΔCT PLs was plotted as % normalized mean fluorescence intensity (MFI) at serially-diluted antibody concentrations. The % normalized MFI values were calculated according to the formula: [MFI-MFI(background)]×100/MFI(saturation)-MFI (background). Error bars indicate the range of values obtained for duplicate samples.

To confirm the native conformation of the gp160ΔCT glycoproteins on the surface of the PLs, we compared the binding of a panel of conformationally-sensitive ligands to gp160ΔCT glycoproteins on PLs with binding to gp160ΔCT glycoproteins expressed on the surface of transiently-expressing cells. The antibodies were selected to probe several faces of the HIV-1 envelope glycoproteins including the neutralization-relevant epitopes overlapping the CD4 binding site (CD4BS). We used the potently neutralizing CD4BS antibody IgG1b12, the less potent neutralizing CD4BS-antibody F105, and soluble CD4 (sCD4) to confirm the correct native conformation of the CD4BS. In addition, we probed gp160ΔCT PLs with the strain-restricted neutralizing V3-loop antibody 39F, and the non-neutralizing antibodies A32 and C11. The binding characteristics of all antibodies to the gp160ΔCT PLs compared to gp160ΔCT glycoproteins expressed on the cell surface were virtually indistinguishable (FIG. 7). The only difference in binding profiles was observed for soluble CD4 (sCD4). For the PLs, sCD4 displayed an almost tenfold higher affinity than it did for gp160ΔCT glycoproteins expressed on cell surfaces. This affinity difference may be a consequence of better exposure of gp160ΔCT glycoproteins on the PLs due to the lack of the cellular glycocalix and cellular protein components. The observed affinities calculated for the antibodies were in the low nanomolar range, consistent with previously reported values (Posner, et al., *J. Acquir. Immune Defic. Syndr.* 6:7-14 (1993); Roben, et al., *J. Virol.* 68:4821-4828 (1994)). For example, the affinity of the antibody IgGb12, as determined by the concentration necessary to achieve half-maximal binding, was calculated to be 6 nM. The affinity of the non-neutralizing C11 antibody was at least 10-fold lower than that of the neutralizing IgG1b12 antibody. This underestimates the affinity difference between the two antibodies because saturation binding was not achieved with the C11 antibody.

CD4 Induction of the 17b Epitope

Figure 8:
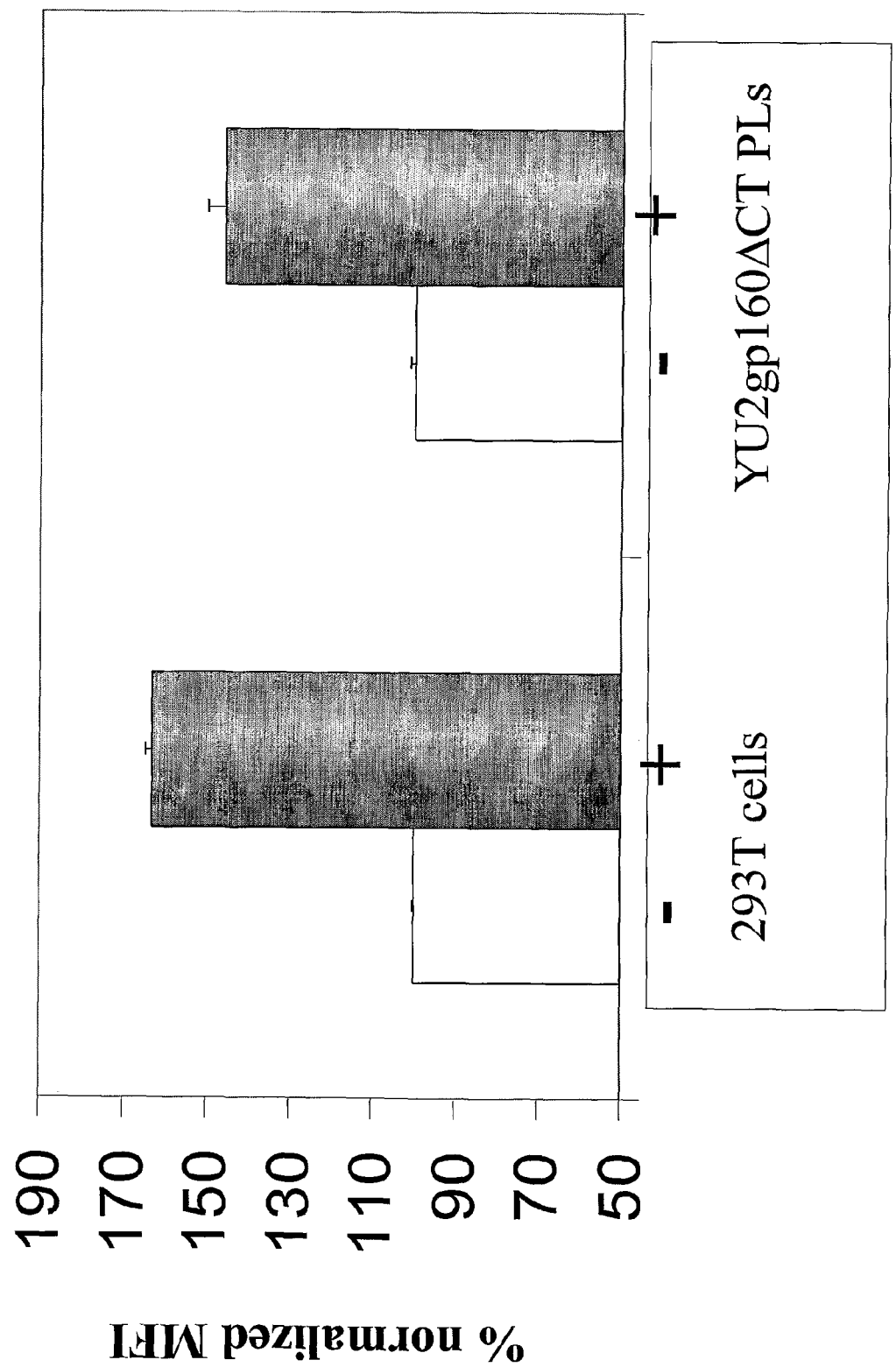
FIG. 8 shows induction of the 17b epitope by sCD4. Binding of the 17b antibody to gp160ΔCT glycoprotein on 293T cells and PLs was compared. Cells and PLs were incubated with and without sCD4 prior to binding of the 17b antibody and analyzed by FACS. Staining without preincubation with sCD4 was set as 100% and increase of 17b binding is shown for 293T cells (open bars) and PLs (solid bars).

One functional conformational change characteristic of native Gp120 is the induction of the 17b antibody epitope by CD4 (Sullivan et al., *J. Virol.* 72:4694-4703 (1998)). To test whether the gp160ΔCT glycoproteins on PLs exhibit this property of gp120 expressed on the cell surface, gp160ΔCT glycoprotein PLs and 293T cells expressing cleavage-competent envelope glycoproteins were preincubated with sCD4 prior to binding of the 17b antibody. 17b binding was detected by staining with a PE-conjugated anti-human IgG antibody followed by FACS analysis. The binding of the 17b antibody was increased by 63% after preincubation with sCD4 on cleavage competent gp160ΔCT glycoprotein expressed on cells compared to a 46% increase on gp160ΔCT PLs (FIG. 8).

Characterization of Cleavage-Deficient gp160ΔCT Glycoproteins

Deletion of the cleavage site for the host protease furin results in the expression of uncleaved gp160ΔCT glycoprotein precursor proteins on the surface of transfected cells. This modification abrogates the dissociation of gp120 from the cell surface and therefore increases the amount of envelope glycoproteins retained on the cell surface or captured on the surface of the PLs. In addition, a cytoplasmic tail deletion was introduced into the gp160 glycoprotein in order to increase cell surface expression (ΔCT). Cell surface expression levels of cytoplasmic tail-deleted envelope glycoproteins increased 8-fold over full-length constructs containing the intact gp160 cytoplasmic tail (data not shown).

Figure 9:
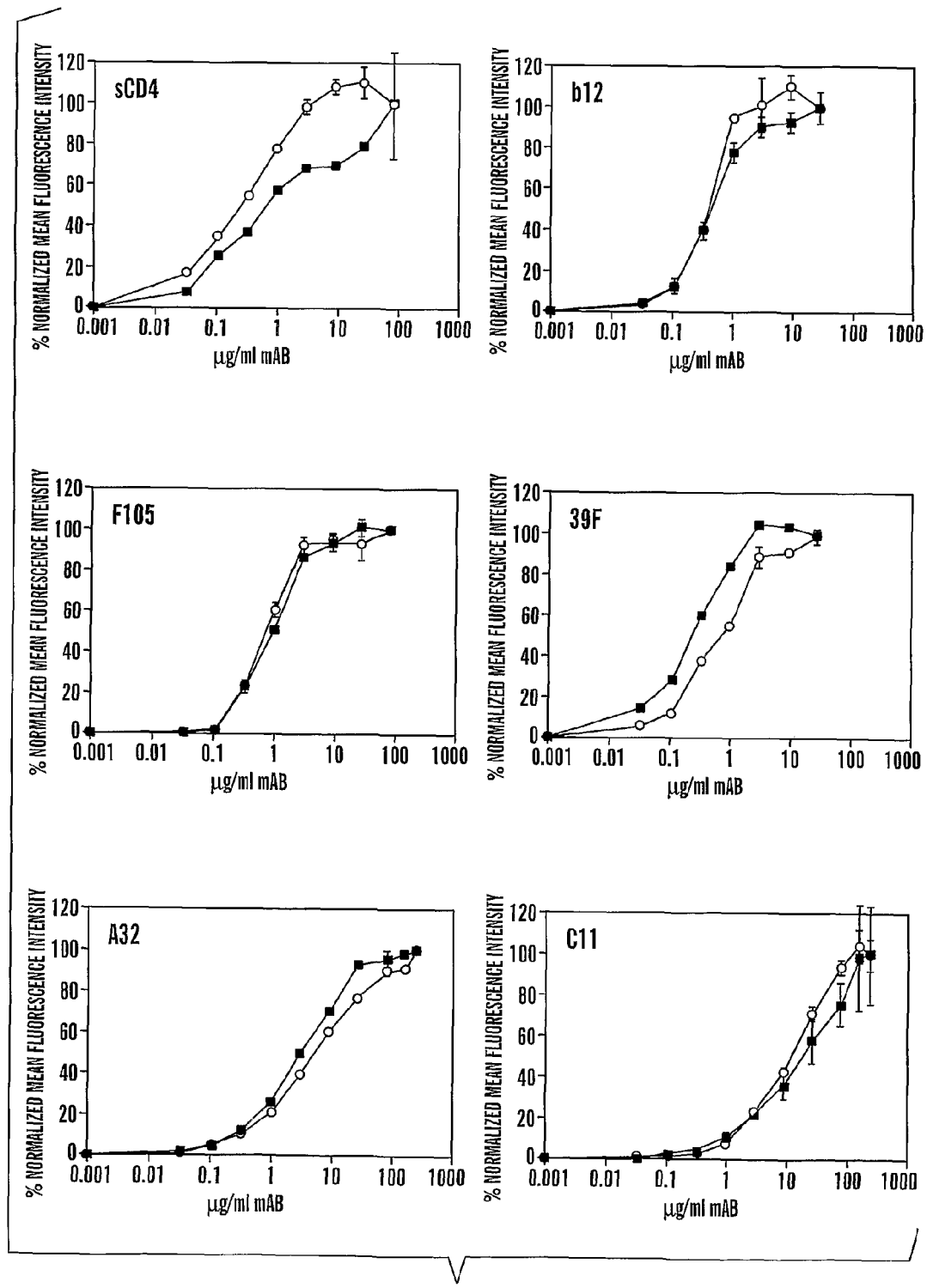
FIG. 9 shows the effect of proteolytic cleavage of HIV-1 envelope glycoprotein on ligand binding. Cleavage-competent YU2 gp160ΔCT glycoprotein (closed squares) and cleavage-defective YU2 gp160ΔCT glycoprotein (open circles) was expressed on 293T cells. Cells were incubated with increasing amounts of the indicated ligands followed by detection with anti-human IgG-PE. The anti-CD4 polyclonal rabbit antibody T45 and anti-rabbit IgG-FITC was used for the detection of sCD4 binding. Normalized MFI was calculated as described for FIG. 7.
Figure 10:
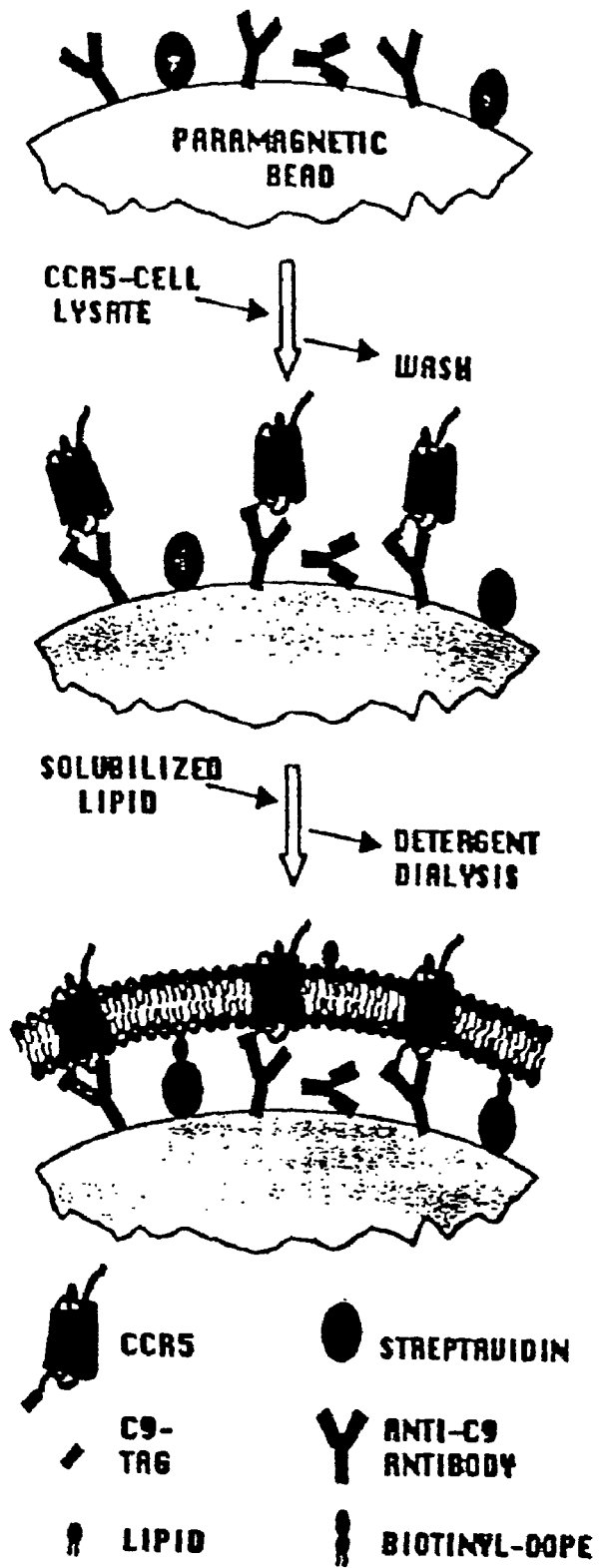
FIG. 10 is a schematic representation of the formation of a paramagnetic CCR5-proteoliposome. The surface of nonporous paramagnetic beads was covalently conjugated with streptavidin and an antibody that recognizes the genetically engineered C-terminal C9 tag on CCR5. The conjugated beads were used to capture the C9-tagged CCR5 from the cell lysate. After extensive washing, the beads were mixed with detergent-solubilized lipid containing approximately 0.1-1% of Biotinyl-DPPE. During the removal of detergent by dialysis, the lipid bilayer membrane self-assembles around the beads and CCR5 is returned to its native lipid environment.

It is possible that the deletion of the cleavage site might distort envelope glycoprotein conformation and result in a conformation not representative of functional, cleaved envelope glycoprotein. To assess the effects of the cleavage site deletion, we analyzed the binding properties of a panel of conformationally-sensitive ligands to cleavage-defective and cleavage-competent gp160ΔCT glycoproteins expressed on the cell surface. FACS analysis was performed by staining the gp160ΔCT expressed on 293T cells with increasing concentrations of ligands. No significant affinity difference was observed between cleavage-competent gp160ΔCT glycoproteins and cleavage-defective envelope glycoproteins for any of the ligands tested (FIG. 9). However, one notable difference in the binding profiles was observed. The binding profile of sCD4 on cells expressing cleavage-competent gp160ΔCT glycoproteins had a biphasic shape. As sCD4 is known to induce shedding of gp120 from envelope glycoprotein complexes (Moore, et al., *Science* 250:1139-1142 (1990)), CD4 binding to the cleavage-competent gp160ΔCT glycoprotein may induce shedding or other conformational changes that result in a biphasic binding profile.

To confirm the processing of the cleavage-competent envelope glycoproteins, 293T cells were transfected with cleavage-competent and -defective envelope glycoprotein constructs. Proteins expressed on the cell surface were iodinated by lactoperoxidase. After detergent lysis and precipitation with the F105 antibody, iodinated proteins were analyzed by SDS-PAGE. The ratio of unprocessed gp160ΔCT precursor proteins to cleaved gp120 was determined to be about 1:1 (data not shown).

Example 2

Proteoliposomes Containing CCR5

Construction and Expression of Codon-optimized CCR5 (synCCR5)

The analysis of codon usage for 45 GPCRs representing different protein subfamilies was performed with GenBank™ data and software developed by the University of Wisconsin Genome Sequence Group. The sequence encoding human CCR5 was optimized for mammalian cell codon usage (Andre, S., et al. (1999). *J. Virology* 72: 1497-1503) utilizing the following codons: alanine (GCC), arginine (CGC), asparagine (AAC), aspartic acid (GAC), cysteine (TGC), glutamic acid (GAG), glutamine (CAG), glycine (GGC), histidine (CAC), isoleucine (ATC), leucine (CTG), lysine (AAG), methionine (ATG), phenylalanine (TTC), proline (CCC), serine (TCC), threonine (ACC), tryptophan (TGG), tyrosine (TAC), and valine (GTG). The 5' and 3' sequences flanking the CCR5 coding sequence were modified. Following restriction sites for EcoRV, EcoRI and HindIII, the Kozak consensus (GCCGCCACC<u>ATGG</u>) (SEQ ID NO: 1) was placed immediately 5' to the CCR5 reading frame. A sequence encoding a single glycine residue followed by the bovine rhodopsin C9 peptide tag (TETSQVAPA) (SEQ ID NO:2) was introduced immediately 5' to the natural stop codon of CCR5. At the 3' end of the epitope-tagged CCR5 gene, XbaI, SalI, and NotI restriction sites were introduced. Analogous constructs were made for the wild-type human CCR5 gene and the bovine rhodopsin gene, except that the codons were not altered and, in the latter case, the C-terminal C9 sequence was naturally present.

A total of 34 oligonucleotides, each approximately 70 nucleotides in length, corresponding to the complete sense and antisense strands of the synCCR5 gene and flanking sequences, were constructed so that approximately 50% of their sequences were complementary to those of each of the two complementary oligonucleotides from the opposite strand. Oligonucleotides were deprotected in pure ammonium hydroxide at 65° C. for 4 h, after which the ammonium hydroxide was evaporated, and the oligonucleotides were dissolved in water at a final concentration of 2 nM. For gene synthesis, the 34 oligonucleotides were separated into five groups (6 or 8 oligonucleotides per group) and 25 cycles of polymerase chain reaction were performed using Pfu polymerase (Stratagene, La Jolla, Calif.) and a 3-fold molar excess of the 5' and 3' terminal oligonucleotides in each group. This step generated five small segments of the synCCR5 gene with complementary and overlapping ends. Equal amounts of each polymerase chain reaction product were combined with a 3-fold molar excess of the 5' and 3' terminal oligonucleotides of the complete synCCR5 sequence. A second round of 25 cycles of polymerase chain reaction yielded the complete synCCR5 sequence. The product was sequenced to ensure that the sequence was correct.

The synCCR5, wild-type CCR5, and bovine rhodopsin sequences were cloned into the following vectors: PMT4 (a gift from Dr. Reeves, Massachusetts Institute of Technology), PACH (a gift from Dr. Velan, Israel Institute for Biological Research), pcDNA 3.1(+) and pcDNA4/HisMax (Invitrogen), and PND (a gift from Dr. Rhodes, University of California, Davis). After cloning of the synCCR5 gene into the pcDNA4/HisMax vector, the sequence encoding the N-terminal HisMax region was removed by QuikChange mutagenesis (Stratagene). Different cell lines were transfected with the synCCR5 and wild-type CCR5 genes using the GenePorter transfection reagent (San Diego, Calif.). Following transfection, cells expressing CCR5 were selected with 0.8 mg/ml of neomycin (G418). Cells expressing the highest surface levels of CCR5 were selected by FACS after staining cells with the R-phycoerythrin-conjugated anti-CCR5 antibody 2D7-PE (Pharmingen, San Diego, Calif.). Among all tested cells (canine thymocytes Cf2Th, human embryonic kidney cells HEK-293T, COS-1, and HeLa (American Type Culture Collection)), the highest CCR5 expression levels were observed in Cf2Th and HEK-293T cells transfected with synCCR5 gene in the PACH vector. The highest synCCR5-expressing clones were selected by FACS from a total of 76 clones of Cf2Th cells and 62 clones of HEK-293T cells.

Radiolabeling and Immunoprecipitation of CCR5

Approximately $4 \times 10^6$ CCR5-expressing Cf2Th or HEK-293T cells grown to full confluency in 100-mm dishes were washed twice in PBS and starved for 1 h at 37° C. in Dulbecco's modified Eagle's medium without cysteine and methionine (Sigma) or in sulfate-free media (ICN, Costa Mesa, Calif.). The starvation medium was removed and 200 TCi each of [$^{35}$S]methionine and [$^{35}$S]cysteine or 500 TCi of [$^{35}$S]sulfate (NEN Life Science Products) in 4 ml of medium was added to the cells for various times for pulse-chase experiments or overnight (12 h) in all other cases. Cells were washed twice with PBS and lysed in 1 ml of solubilization medium composed of 100 mM $(NH_4)_2 SO_4$, 20 mM Tris-HCl (pH 7.5), 10% glycerol, 1% (w/v) detergent (see below), and Protease Inhibitor Mixture (one tablet of Complete™ (Roche Molecular Biochemicals) per 25 ml). The lysate was incubated at 4° C. for 30 min on a rocking platform, and cell debris was removed by centrifugation at 14,000×g for 30 min. CCR5 was precipitated with 20 1 1 of 1D4-Sepharose beads (Reeves, P., Thurmond, R. L., and Khorana, G. G. (1996) *Proc. Natl. Acad. Sci. USA* 4: 7784-90) overnight, after which the beads were washed six times in the solubilization medium and pelleted. An equal volume of 2×SDS-sample buffer was added to the beads, followed by resuspension and incubation for 1 h at 55° C. Samples were run on 11% SDS-polyacrylamide minigels, which were visualized by autoradiography or analyzed on a Molecular Dynamics PhosphorImager SI (Sunnyvale, Calif.).

A total of 18 detergents were tested in the solubilization buffers. The detergents, with abbreviations and critical micelle concentrations in parentheses, were n-octyl-β-D-glucopyranoside (23.4 mM), n-decyl-β-D-maltoside (1.8 mM), n-dodecyl-β-D-maltoside (DDM) (0.17 mM), cyclohexyl-butyl-β-D-maltoside (Cymal™-4, 7.6 mM), cyclohexyl-pentyl-β-D-maltoside (Cymal™-5, 2.4 mM), cyclohexyl-hexyl-β-D-maltoside (Cymal™-6, 0.56 mM), cyclohexyl-heptyl-β-D-maltoside (Cymal™-7, 0.19 mM), cyclo-hexylpropanoyl-N-hydroxyethylglucamide (108 mM), cyclohexylbutanoyl-N-hydroxyethylglucamide (35 mM), cyclohexylpentanoyl-N-hydroxyethyglucamide (11.5 mM), N-octylphosphocholine (Fos-Choline™ 8, 114 mM), N-decylphosphocholine (Fos-Choline™ 10, 11 mM), N-dodecylphosphocholine (Fos-Choline™ 12, 1.5 mM), N-tetradecylphosphocholine (Fos-Choline™ 14, 0.12 mM), Triton X-100 (0.02 mM), CHAPS (8 mM), Nonidet P-40 (0.02 mM), and diheptanoyl-phosphocholine (DHPC) (1.4 mM). All detergents were purchased from Anatrace (Maumee, Ohio) except DHPC, which was purchased from Avanti Polar Lipids (Alabaster, Ala.).

Purification of CCR5

Stable Cf2Th/PACH/synCCR5 cells grown to full confluency in a 150-mm dish were incubated with medium containing 4 mM sodium butyrate for 40 h, washed in PBS, detached by treatment with 5 mM EDTA/PBS, pelleted, and again washed in PBS. Cells were solubilized for 30 min with 3 ml of the solubilization medium containing Cymal™-5 and centrifuged for 30 min at 14,000×g. The cell lysate was incubated with 50 1 1 of 1D4-Sepharose beads on a rocking platform at 4° C. for 10-12 h. The Sepharose beads were washed five times with the washing buffer (100 mM $(NH_4)_2SO_4$, 20 mM Tris-HCl (pH 7.5), 10% glycerol, and 1% Cymal™-5) and once with washing buffer plus 500 mM $MgCl_2$. CCR5 was eluted from the beads by three successive washes with 50 1 1 of medium containing 200 1M C9 peptide (SEQ ID NO:2) (TETSQVAPA), 500 mM $MgCl_2$, 100 mM $(NH_4)_2SO_4$, 20 mM Tris-HCl (pH 7.5), 10% glycerol, and 0.5% Cymal™-5. The total quantity of harvested CCR5 was estimated by Coomassie Blue staining of an SDS-polyacrylamide gel run with standard quantities of bovine serum albumin.

Binding of HIV-1 gp120 Envelope Glycoproteins to Solubilized CCR5

Approximately $4\times10^6$ Cf2Th/PACH/synCCR5 cells were labeled for 12 h with [$^{35}$S]Met/Cys and lysed in solubilization buffer containing 1% Cymal™-5. One ml of cleared cell lysate was incubated with 100-500 1 1 of the gp120-containing solutions. The unlabeled JR-FL gp120 was produced in *Drosophila* cells (Wu, L., et al. (1996), *Nature* 384, 179-183), and the ADA and 190/197 R/S gp120 glycoproteins were produced from transiently transfected 293T cells that had been radiolabeled with [$^{35}$S]Met/Cys overnight. Except in the case of the CD4-independent gp120 variant, 190/197 R/S, the gp120 glycoproteins (2-4 1 g) were preincubated with sCD4 (2-4 1 g) in 20 ml of PBS for 1 h at 22° C. prior to addition to the CCR5-containing lysates. After 12 h at 4° C., the gp120-CCR5 complexes were precipitated with either the C11 anti-gp120 antibody (kindly provided by Dr. James Robinson, Tulane University Medical School) or with the 1D4 antibody.

Expression of CCR5 in Mammalian Cells

We compared the codon usage for opsins, the only GPCRs that are naturally highly expressed, with the codon usage for 45 other GPCRs representing a spectrum of different GPCR subfamilies. Opsin codons are biased toward those shown to be optimal for efficient translation in mammalian cells (Andre, S., et al (1998), *J. Virol.* 72: 1497-1503), whereas other GPCRs, including CCR5, are associated with codons that are more random and, in many cases, inefficiently translated (data not shown). A codon-optimized CCR5 gene was designed, synthesized using the polymerase chain reaction, and transiently expressed in several different cell lines, using five different expression vectors (pcDNA 3.1, PACH, PND, PMT4, and pcDNA4/HisMax). The level of CCR5 expression directed by the codon-optimized gene was 2-5 times that directed by the wild-type CCR5 gene. Among the cell lines tested, CCR5 expression was the highest in Cf2Th canine thymocytes (data not shown), so these cells were used to generate stable cell lines. The PACH vector was used to express the codon-optimized gene encoding human CCR5 containing a 9-residue C-terminal epitope tag (the C9 tag) derived from bovine rhodopsin. The presence of the C9 tag allows recognition of the CCR5 protein by the 1D4 antibody (Oprian, D. D., et al. (1987), *Proc. Natl. Acad. Sci. U.S.A.* 84: 8874-8878). CCR5 expression in the stable cell line, designated Cf2Th/PACH/synCCR5, could be enhanced 2-3 fold by treatment of the cells with sodium butyrate. Following this treatment, approximately 3-5 1 g of CCR5 of high purity could be isolated from $10^7$ Cf2Th/PACH/synCCR5 cells, using techniques described below.

Precursor and Mature Forms of CCR5

CCR5 synthesis and turnover in Cf2Th cells were studied by pulse-chase analysis. A precursor of approximately 40 kDa chased into the mature form of CCR5, which migrated as a wide band of approximately 43 kDa. The CCR5 precursor exhibited a half-life of approximately 25 min. The half-life of the mature form of CCR5 was 11-14 h, regardless of whether CCR5 expression was directed by the wild-type or codon-optimized CCR5 gene. The half-lives of the precursor and mature forms of CCR5 in HEK-293 cells were similar to those in Cf2Th cells (data not shown). In several different cell lines, a lower molecular mass (approximately 36 kDa) form of CCR5 appeared in parallel with the mature protein. This lower molecular mass form of CCR5 was expressed at lower levels than the mature form of CCR5 and has not been completely characterized. Its identity as a CCR5 isoform was confirmed by its precipitation by the 1D4 antibody and the anti-CCR5 antibody 2D7 and by mass spectrometry.

Solubilization of Native CCR5

Membrane protein purification requires solubilization of the membranes, typically through the use of detergents. A broad spectrum of conditions was studied to arrive at the composition of the buffer that allowed solubilization and isolation of native CCR5. This optimization was guided by a comparison of the amount of solubilized CCR5 capable of being precipitated by the 2D7 antibody, which recognizes a conformation-dependent CCR5 epitope (Wu, L., et al. (1997), *J. Exp. Med.* 186: 1373-1381), with that able to be precipitated by the 1D4 antibody directed against the linear C9 epitope tag. In this manner, the percentage of solubilized CCR5 remaining in a native conformation could be estimated. Eighteen detergents, most of which were designed specifically for the extraction and purification of membrane proteins, were studied. In terms of the quantity of isolated CCR5 protein, as well as the percentage of protein in a conformation able to be recognized by the 2D7 antibody, the most effective detergents were DDM, Cymal™-5, and Cymal™-6. Of these detergents, Cymal™-5 exhibits the highest critical micelle concentration (2.4 mM), facilitating dialysis of the detergent from the protein solution for the purposes of membrane reconstitution and/or crystallization. We also found that a CCR5 conformation competent for binding HIV-1 gp120 was best preserved in buffers containing Cymal™-5 (see below). Therefore, Cymal™-5 was used for further refinement of the CCR5 solubilization/isolation protocol, examining a number of variables (salt composition and concentration, pH, temperature, and minor additives) known to influence the stability of solubilized proteins (Hamaguchi, K. (1992) *The Protein Molecule. Conformation, Stability and Folding*, Japan Scientific Societies Press, Springer-Verlag, N.Y.). Ammonium sulfate and glycerol were found to prolong the existence of a CCR5 conformation capable of being recognized by the 2D7 antibody (data not shown). The optimized CCR5 solubilization buffer was composed of 100 mM $(NH_4)_2SO_4$, 20 mM Tris-HCl (pH 7.5), 10% glycerol, and 1% Cymal™-5.

CCR5-Expressing Cells.

The cell line (Cf2Th/CCR5) stably expressing approximately $10^6$ molecules of CCR5 per cell was generated by transfection of Cf2Th canine thymocytes with the above-described codon-optimized CCR5 gene. The C-terminus of the expressed CCR5 consists of a glycine residue followed by the C9 nonapeptide TETSQVAPA (SEQ ID NO: 2), which contains the epitope for the 1D4 antibody. Wild-type and C-terminally tagged CCR5 molecules have been shown to be functionally comparable. Cf2Th/CCR5 cells grown to full confluency in 150 mm dishes were harvested using 5 mM EDTA in PBS, washed in PBS, pelleted and frozen until needed.

Radiolabeling of Cells Expressing CCR5 or gp120.

Cf2Th/CCR5 cells were radiolabeled in 150 mm dishes for 12 hours with 10 ml/dish of Met-Cys-free DMEM supplemented with 400 Ci each of $^{35}$S-methionine and $^{35}$S-cysteine (NEN Life Science Products, Boston, Mass.). Labeled cells were harvested using 5 mM EDTA in PBS, pelleted and frozen until needed.

To label the HIV-1 gp120 envelope glycoprotein, HEK-293T cells (American Type Culture Collection) grown to 70-80% confluence were transfected (Geneporter transfection reagent, Gene Therapy Systems, San Diego, Calif.) with plasmids expressing secreted gp120 from HIV-1 strains ADA and HXBc2 (ref. Kolchinsky). Twenty-four hours after the transfection, the medium was replaced with labeling medium, as described above. The cell supernatants containing $^{35}$S-cysteine/methionine-labeled gp120 were harvested every 48 hours a total of three times. The labeled gp120 was purified from the pooled supernatants using a Protein A Sepharose-F105 antibody column, as described (ref. Wu et al).

Coating of Dynabeads by Antibodies and Streptavidin.

Tosylactivated Dynabeads® M-280 (Dynal, Inc., Lake Success, N.Y.) were conjugated with 1D4 antibodies (National Cell Culture Center, Minneapolis, Minn.), and streptavidin (Vector Laboratories, Inc., Burlingame, Calif.) at a molar ratio 10:1 unless specifically mentioned. Approximately $6 \times 10^8$ beads in 1 ml volume were vortexed, pelleted on a magnetic separator (Dynal) and resuspended in 1 ml of binding buffer (0.1 M sodium phosphate, pH 7.4) containing 1 mg of 1D4 antibody and 30 Tg of streptavidin. After incubation on a rocking platform for 20 hours at 37° C., the unbound surface reactive groups on the beads were inactivated by treatment with 0.2 M Tris-HCl (pH 8.5) for 4 hours at 37° C. The noncovalently absorbed proteins were removed by a one-hour incubation in medium composed of 1% cyclohexyl-pentyl-ã-D-maltoside (Cymal™-5) detergent (Anatrace, Maumee, Ohio), 20 mM Tris-HCl (pH 7.5), 100 mM $(NH_4)_2SO_4$ and 1M NaCl. Then the 1D4/streptavidin-beads were washed twice and stored at 4° C. in PBS. The efficiency of antibody conjugation to the beads, which was estimated by FACS using anti-mouse R-phycoerythrin-conjugated IgG (IgG-PE) (Boehringer Mannheim, Indianapolis, Ind.), was approximately $5 \times 10^4$ antibody molecules/bead. The 2D7/Streptavidin conjugation was accomplished using the same protocol.

Preparation of Lipid Solutions for Liposomal Membrane Reconstitution.

All lipids were obtained as chloroform solutions from Avanti Polar Lipids (Alabaster, Ala.). A total of 10 mg of chloroform-dissolved lipids 1-Palmitoyl-2-Oleoyl-sn-Glycero-3-Phosphocholine (POPC), 1-Palmitoyl-2-Oleoyl-sn-Glycero-3-Phosphoethanolamine (POPE) and Dimyristoylphosphatidic acid (DMPA), mixed in a molar ratio of 6:3:1, were dried in a 2-ml polyethylene tube under a vacuum until all of the solvent was removed. One milliliter of PBS was added to the tube and a liposomal solution was obtained by 1-2 min ultrasonication in an ice bath using the Ultrasonic Processor (Heat Systems, Inc., Farmingdale, N.Y.). Liposomal solutions of total lipids from membranes of Cf2Th cells, which were extracted with chloroform/methanol (ref. Folch), were prepared similarly, using a final lipid concentration of 10 mg/ml. Liposomal solutions of the head group-modified synthetic lipids dipalmitoylphosphoethanolamine-N-Biotinyl (Biotinyl-DPPE) and dioleoylphosphoethanolamine-Lissamine Rhodamine B (Rho-DOPE), at a final concentration of 1 mg/ml, were prepared separately using the same protocol. All liposomal solutions were kept in liquid $N_2$ until use.

Formation of Proteoliposomes with Purified CCR5.

Approximately $10^8$ Cf2Th/CCR5 cells were lysed in 10 ml of solubilization buffer (S-buffer) composed of 100 mM $(NH_4)_2SO_4$, 20 mM Tris-HCl (pH 7.5), 10% Glycerol, 0.5% (w/v) Cymal™-5 and Protease Inhibitor Mixture (one tablet of Complete™ (Boehringer Mannheim) per 50 ml) for 30 minutes at 4° C. Cell debris was removed by 30 min centrifugation at 150,000×g. Approximately $5 \times 10^8$ 1D4/Streptavidin-coated beads washed in S-buffer were added to the cleared cell lysate and incubated in it for 1 h at 4° C. on a rocking platform. The CCR5-bound beads were then removed from the cell lysate and extensively washed in S-buffer. For formation of the lipid membrane around the CCR5-containing beads, 1 mg of liposomes composed of either synthetic lipid mixtures or Cf2Th cellular lipids was combined with 10 μg of liposomes made from Biotinyl-DPPE and solubilized in 1 ml S-buffer. When fluorescent labeling of the lipid membrane was desired, 10 μg of Rho-DOPE was added to the mixture. This detergent-containing mixture was added to CCR5-containing beads and, after 1 hour incubation at 4° C., the detergent was slowly removed by dialysis for 24 hours at 4° C. in 12,000-kDa dialysis tubing against 100 mM $(NH_4)_2SO_4$, 20 mM Tris-HCl (pH 7.5) and 10% glycerol. The excess of unbound lipid and residual detergent was removed on a magnetic separator and proteoliposomes were stored in PBS at 4° C. for up to two months.

The protein composition of CCR5-proteoliposomes was analyzed by silver staining or, when $^{35}$S-cysteine/methionine-labeled CCR5 was used, by autoradiography. For these purposes, $10^7$ proteoliposomes were resuspended in 2% SDS-sample buffer and, after 1 hour incubation at 55° C., the eluted sample was run on an 11% polyacrylamide mini-gel under reducing conditions.

Ligand Binding to CCR5-Proteoliposomes.

The binding of the 2D7 anti-CCR5 antibody was analyzed by FACS and confocal microscopy, using 2D7 conjugated with R-phycoerythrin (2D7-PE). CCR5-proteoliposomes were suspended in 5% BSA fetal calf serum in PBS or, in some experiments, in binding buffer (see below) and incubated with 2D7-PE for one hour at 22° C. The proteoliposomes were then washed in the same buffer, fixed in 2% formaldehyde in PBS, and analyzed by FACS or confocal microscopy.

The binding of the HIV-1 gp120 glycoprotein to CCR5-proteoliposomes was analyzed by FACS using unlabelled gp120 (JR-FL strain) or by SDS-polyacrylamide gel analysis of bound, radiolabeled gp120 proteins. For the FACS analysis, CCR5-proteoliposomes were suspended in 0.5 ml binding buffer (150 mM NaCl, 5 mM CaCl$_2$, 2 mM MgCl2, 20 mM Tris, pH 7.5) and incubated for one hour at 22° C. with 3-5 šg JR-FL gp120 or with JR-FL gp120 that had been preincubated for one hour at 37° C. with an equimolar concentration of sCD4. Afterwards, the anti-gp120 antibody C11 (kindly provided by Dr. James Robinson, Tulane University) and a fluorescein-conjugated goat anti-human IgG (Pharmingen) were added, each at a final concentration of 3-5 Tg/ml. Following incubation at 22° C. for one hour, the CCR5-proteoliposomes were washed in the binding buffer, fixed in 2% formaldehyde in PBS, and used for FACS and confocal microscopy.

For the studies of radiolabeled HIV-1 gp120 binding to CCR5-proteoliposomes, the metabolically labeled gp120 glycoproteins from a CCR5-using HIV-1 strain, ADA, and from a CXCR4-using HIV-1 strain, HXBc2, were employed. In a preferred embodiment, one would use a radiolabelled HIV-1 gp120 proteoliposome to look at binding to the CCR5 proteoliposomes. The gp120 glycoproteins were incubated in either the presence or absence of sCD4 (10 nM final concentration) for one hour at 37° C. Approximately 10$^7$ CCR5-proteoliposomes were resuspended in 1 ml of binding buffer and incubated with the gp120 glycoproteins for 1 hour at 22° C. The proteoliposomes were extensively washed in the binding buffer and then resuspended in SDS-sample buffer containing 5%-mercaptoethanol. After boiling for 2 minutes, the samples were loaded on 10% polyacrylamide mini-gels and analyzed by autoradiography.

Protein Composition of CCR5-Proteoliposomes

To examine the cellular proteins incorporated into the proteoliposomes, Cf2Th-CCR5 cells were metabolically labeled with $^{35}$S-cysteine and $^{35}$S-methionine and used for proteoliposome formation. The proteoliposomes were incubated in SDS-sample buffer at 55° C. for one hour and the labeled proteins analyzed on polyacrylamide gels. Prominent bands associated with mature CCR5 (43 kDa) and a previously seen CCR5 derivative (36 kDa) were observed, as well as faint bands associated with higher-molecular weight aggregates of CCR5. Other cellular proteins were apparently present at only trace levels. These results indicate that CCR5 is the major cellular protein in the proteoliposomes.

The proteins in the paramagnetic proteoliposomes were also examined by silver staining of polyacrylamide gels of the SDS lysates. The only other bands visible in addition to the CCR5 bands described above were those associated with the 1D4 antibody heavy and light chains (55 and 25 KDa, respectively) and streptavidin (60 KDa) (data not shown). This demonstrates that apparently, no cellular proteins other than CCR5 are incorporated stoichiometrically into the paramagnetic proteoliposomes.

Analysis of the Lipid Bilayer Membrane in CCR5-Proteoliposomes

Figure 11:
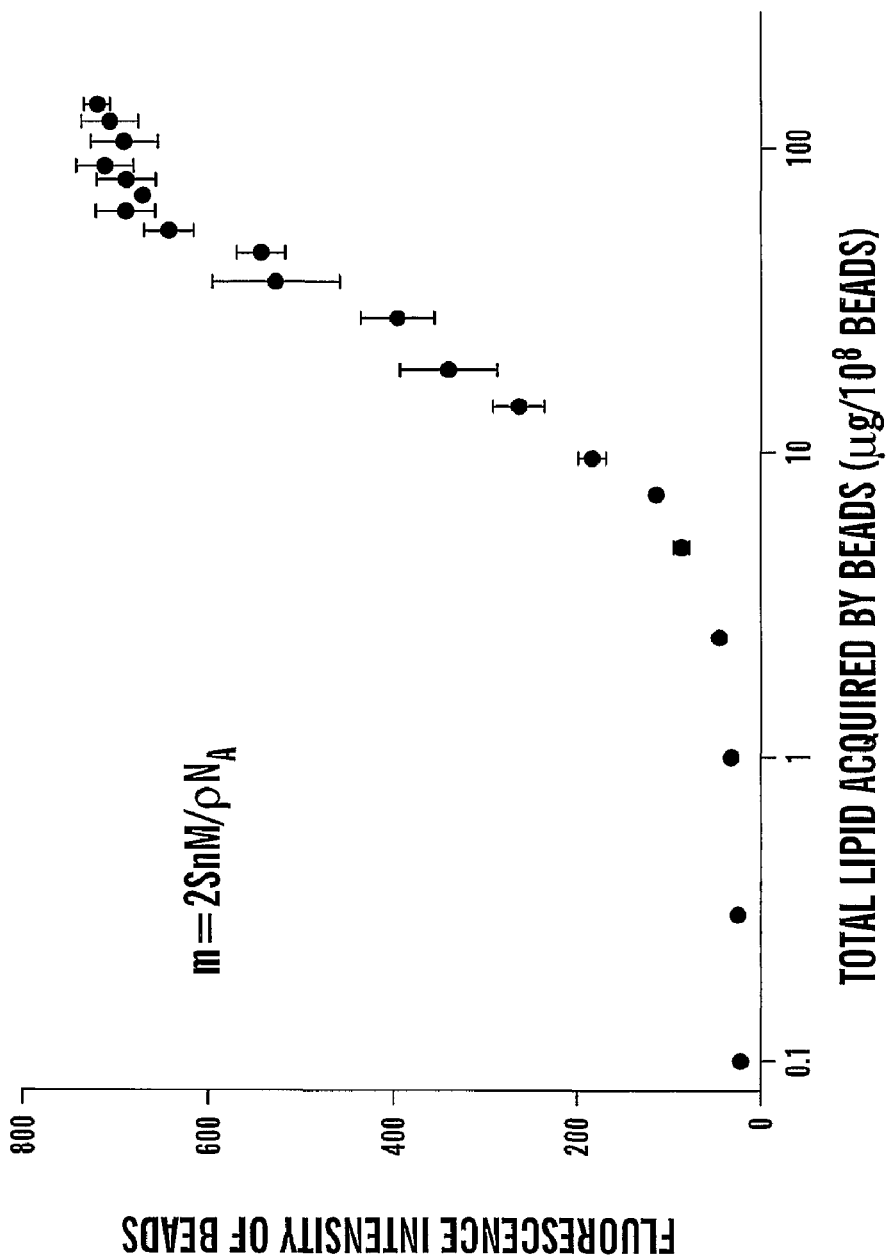
FIG. 11 shows quantitation of the lipid acquired by paramagnetic CCR5-proteoliposome beads. Approximately 10⁸ 1D4/Streptavidin-conjugated beads were reconstituted with CCR5 and different quantities of lipids. The lipid mixtures contained POPC/POPE/DPPA in a 6:3:1 molar ratio, as well as 1% each (by weight) of biotinyl-DPPE and rhodamine-DOPE. The intensity of lissamine rhodamine B fluorescence, which was measured by FACS, exhibited a mean value of 20,000 counts. The data points shown represent the average of three independent experiments, with standard deviations indicated. In the inset is the formula by which the approximate mass of total lipid (m) necessary for complete encapsulation of given number of beads (n) by a single lipid bilayer membrane was calculated. S is the estimated effective surface of the 2.5-micrometer diameter Dynal bead. The approximate area occupied by one lipid molecule in the bilayer membrane (P) was considered to be 60 Å². $N_A$ is Avogadro's number and M the average molecular weight of the lipids used for membrane reconstitution.

The total quantity of lipid incorporated into the proteoliposomes was determined. FACS analysis of CCR5-proteoliposomes formed with increasing amounts of lipid containing 1% rhodamine-DOPE revealed that approximately 80-90 Tg of lipid was acquired per 10$^8$ beads (FIG. 11). This is higher than the amount of lipid (approximately 40 Tg) that is theoretically needed to form bilayers surrounding beads of 2.8 Tm diameter (see formula in FIG. 11, inset). This difference can be explained by the irregularity of the bead surface, which was documented by scanning electron microscopy (data not shown), and which could contribute to the formation of small micelle-like structures in the crevasses of the bead surface. Additionally, some of the input lipid may have been lost during dialysis.

The CCR5-proteoliposomes were also studied by confocal microscopy. The control paramagnetic beads did not exhibit fluorescence indicative of rhodamine-DOPE incorporation. By contrast, the CCR5-proteoliposomes that had been formed with 1% rhodamine-DOPE fluoresced intensely and uniformly. No lipid vesicles or other structures greater than 0.1 μm were observed on the surface of the fluorescently labeled CCR5-proteoliposomes. These data are consistent with the CCR5-proteoliposomes being surrounded by a single lipid bilayer membrane with at most small irregularities.

Ligand Binding Properties of CCR5-Proteoliposomes

CCCR5-proteoliposomes efficiently bound the 2D7 antibody, which recognizes a conformation-dependent epitope on the CCR5 ectodomain.

To examine the ability of the CCR5-proteoliposomes to bind the HIV-1 exterior envelope glycoprotein, the gp120 glycoprotein from the CCR5-using strain JR-FL was preincubated with a soluble form of CD4 (sCD4) to induce the high-affinity interaction with CCR5. The gp120/sCD4 complex was incubated with CCR5-proteoliposomes, after which the bound complexes were detected by the C11 anti-gp120 antibody. Binding of the gp120 glycoprotein/sCD4 complexes to the CCR5-proteoliposomes, but not to control proteoliposomes lacking CCR5, was readily detected.

The binding of the HIV-1 gp120 glycoprotein to the CCR5-proteoliposomes was also examined in a different assay. Equivalent amounts of metabolically labeled gp120 glycoproteins from an HIV-1 strain, HXBc2, which does not use the CCR5 protein as a coreceptor, and from the ADA strain, which uses CCR5 as a coreceptor, were added to the CCR5-proteoliposomes. Only the ADA gp120 glycoprotein detectably bound the CCR5-proteoliposomes. This binding was enhanced by the addition of sCD4. The binding of the ADA gp120/sCD4 complex to the CCR5-proteoliposomes was inhibited by preincubation of the proteoliposomes with the 2D7 anti-CCR5 antibody. These results indicate that the gp120 glycoprotein from a CCR5-using HIV-1 specifically binds CCR5 in the proteoliposome, and that CD4 binding enhances the gp120-CCR5 interaction, as has been observed with cell surface CCR5 (Wu, L. et al. (1996) *Nature* 384: 179-183; Trkola, A. et al. (1996), *Nature* 384: 184-187).

Stability of CCR5-Proteoliposomes

The effects of alterations in pH, ionic strength and temperature on the stability of the CCR5-proteoliposomes were examined. Rhodamine-DOPE-labeled CCR5-proteoliposomes were exposed to acidic (pH=3) or basic (pH=10) conditions for 30 minutes, after which they were returned to a neutral pH environment. The fluorescence intensity measured by FACS was comparable to that observed for untreated control CCR5-proteoliposomes (data not shown). Fluorescence intensity was also not affected by incubation in solutions of different ionic strengths, ranging from less than 1 mM to 3M NaCl (data not shown). The binding of the 2D7 antibody to CCR5-proteoliposomes was completely disrupted by incubation of the antibody-proteoliposome complex at pH 3.0 for 30 minutes. However, the ability of the 2D7 antibody to rebind the CCR5-proteoliposomes was completely restored by returning the pH to 7.0. The CCR5-proteoliposomes were stable at temperatures up to 50° C. for short periods of time (less than two hours) and could be stored for at least two months in PBS at 4° C. without loss of binding properties.

We have thus shown that an integral membrane protein such as the GPCR CCR5 can be expressed at reasonably high levels in mammalian cells and purified in its native state in detergent-containing solutions. We have shown that the purified CCR5 can be reconstituted into a native lipid membrane environment formed on the surface of paramagnetic beads. Accordingly, with minor adjustments, the approach is applicable to many integral membrane proteins.

Example 3

Proteoliposomes Containing CXCR4

Purification of CXCR4 Proteoliposomes

CXCR4-Cf2Th cells were grown to full confluency in 100 mm cell culture dishes. Cells were detached from the dish with 1×PBS/5 mM EDTA and pelleted in microcentrifuge tubes at 1×10$^8$ cells/pellet. The pellet was resuspended in an ice cold buffer containing 100 mM (NH4)2SO4, 20 mM Tris pH 7.5, 20% glycerol, 1× Complete (Roche) protease inhibitor cocktail and 1% of either CHAPSO (Anatrace) or Cymal-7 (Anatrace). Resuspended cells were incubated for 5 minutes on ice followed by 25 minutes at 4° C. on a Nutator (Fisher Scientific). After incubation, cell debris was removed by centrifugation at 14,000×g for 30 minutes at 4° C. The supernatant was transferred to a new microcentrifuge tube and 5×10$^8$ 1D4 conjugated M-280 Dynal beads were added. Cell lysate was incubated with beads for 2.5 hours at 4° C. on a Nutator. The tube was then placed in a Dynal MPC-S magnet to remove the beads. The beads were washed two times with ice cold washing buffer (either 1% CHAPSO or Cymal-7, 100 mM (NH4)$_2$SO$_4$, 20 mM Tris pH 7.5 and 20% glycerol). After washing, beads prepared with CHAPSO were resuspended in 2.5 ml of ice cold CHAPSO washing buffer containing 1.5 mg 1-Palmitoyl-2-Oleoyl-sn-Glycero-3-Phosphocholine, 0.75 mg 1-Palmitoyl-2-Oleoyl-sn-Glycero-3-Phosphoethanolamine, 0.225 mg 1.2 Dioleoyl-sn-Glycero-3-Phosphate and 0.025 mg Biotinyl-Phosphoethanolamine. Cymal-7 prepared beads were resuspended in ice cold 1% Cymal-5 washing buffer containing the above described lipids. The solution was then injected into a Slide-A-Lyzer (Pierce, 10 kDMWCO) and dialyzed for 24 hours against washing buffer containing no detergent at 4° C. The samples were dialyzed in a specially designed machine that constantly rotated the Slide-A-Lyzer to prevent settling of the beads. Following dialysis, the paramagnetic proteoliposomes were removed from the Slide-A-Lyzer and washed two times in 1×PBS/2% FBS to remove unbound lipid and any remaining detergent. Proteoliposomes were stored in 1×PBS/2% FBS/0.02% sodium azide for up to two months at 4° C.

Figure 12:
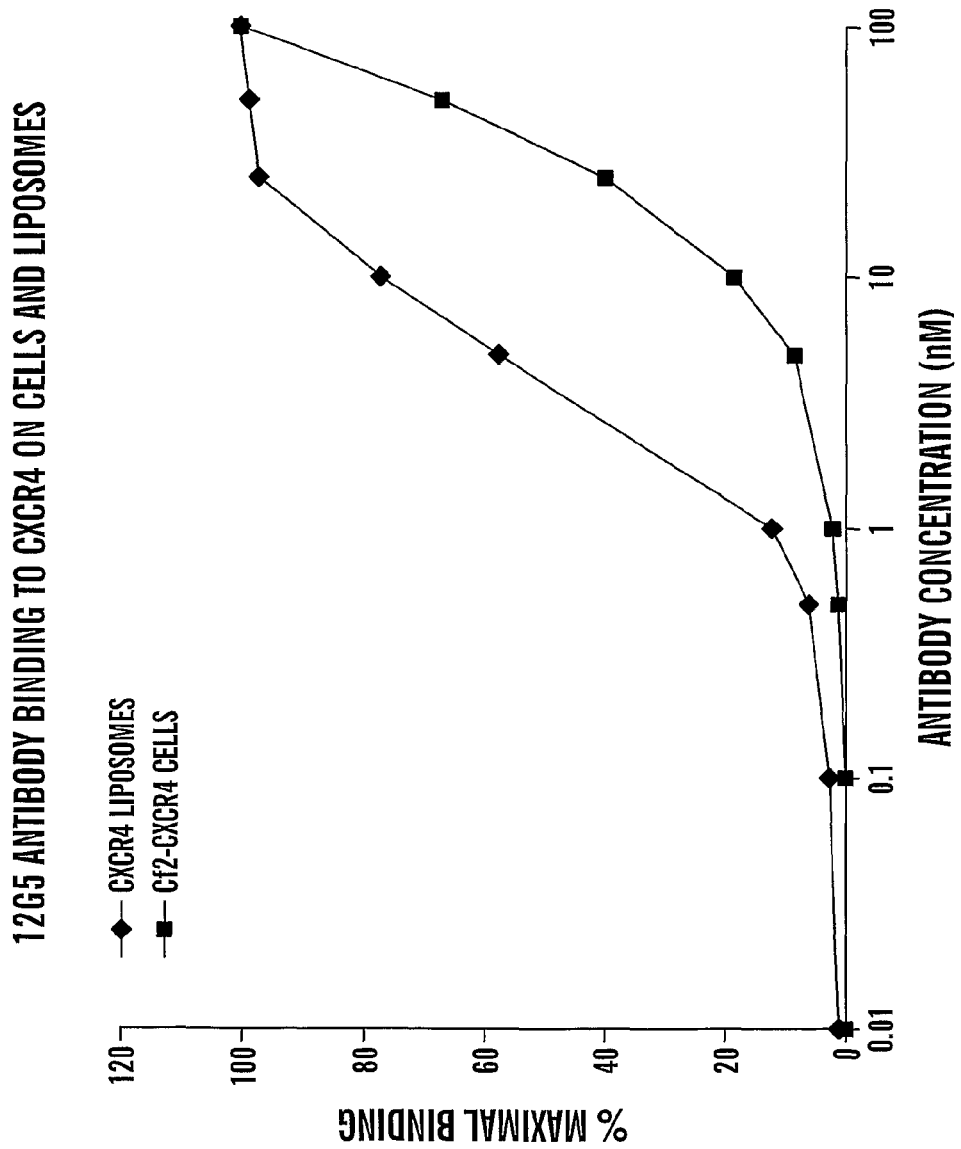
FIG. 12 shows binding of the 12G5 antibody to CXCR4-proteoliposomes and to CXCR4-expressing cells. CXCR4-proteoliposomes were prepared as described in the text from cells expressing human CXCR4 with a C-terminal C9 tag. The binding of the 12G5 antibody, which recognizes a conformation-dependent structure on CXCR4, to the CXCR4-expressing cells and CXCR4-proteoliposomes is shown. The apparent affinity of the 12G5 antibody for the CXCR4 on the proteoliposome surface is at least as good as that for CXCR4 on cells. A similar result was obtained for the conformation-dependent, CXCR4-directed antibody FAB173 (data not shown).

FIG. 12 shows binding of the 12G5 antibody to CXCR4-proteoliposomes and to CXCR4-expressing cells. CXCR4-proteoliposomes were prepared as described in the text from cells expressing human CXCR4 with a C-terminal C9 tag. The binding of the 12G5 antibody, which recognizes a conformation-dependent structure on CXCR4, to the CXCR4-expressing cells and CXCR4-proteoliposomes is shown. The apparent affinity of the 12G5 antibody for the CXCR4 on the proteoliposome surface is at least as good as that for CXCR4 on cells. A similar result was obtained for the conformation-dependent, CXCR4-directed antibody FAB173 (data not shown).

Figure 13:
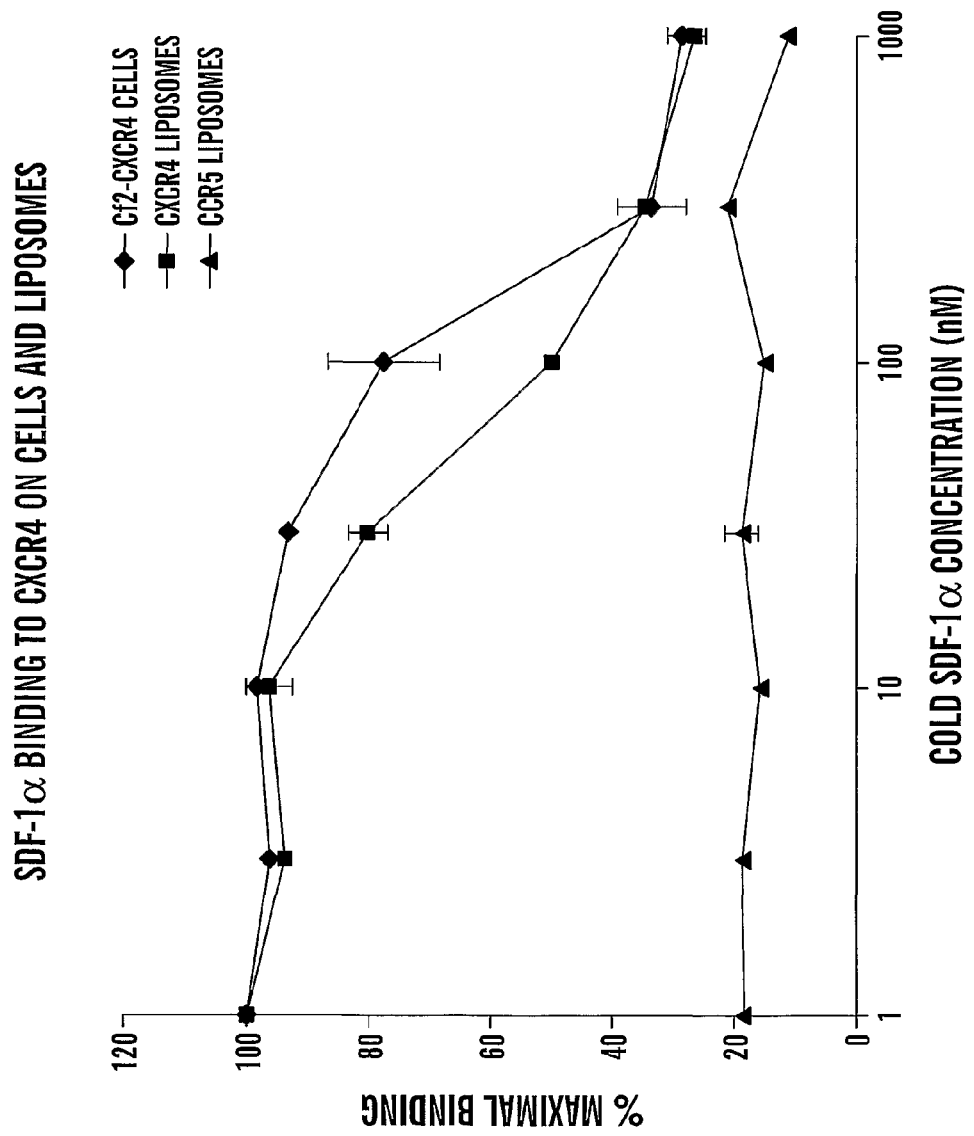
FIG. 13 shows binding of SDF-1α to CXCR4 on cells and proteoliposomes. Radiolabeled SDF-1α, the natural CXCR4 ligand, was incubated with either CXCR4-expressing cells or proteoliposomes bearing CXCR4 or CCR5. Unlabeled (cold) SDF-1α was added in increasing amounts, and the amount of radiolabeled SDF-1α bound to the cells or proteoliposomes was measured. The SDF-1α bound with high affinity to the CXCR4-expressing cells and CXCR4-proteoliposomes, but not to the CCR5-proteoliposomes.

FIG. 13 shows binding of SDF-1α to CXCR4 on cells and proteoliposomes. Radiolabeled SDF-1α, the natural CXCR4 ligand, was incubated with either CXCR4-expressing cells or proteoliposomes bearing CXCR4 or CCR5. Unlabeled (cold) SDF-1α was added in increasing amounts, and the amount of radiolabeled SDF-1α bound to the cells or proteoliposomes was measured. The SDF-1α bound with high affinity to the CXCR4-expressing cells and CXCR4-proteoliposomes, but not to the CCR5-proteoliposomes.

Example 4

Screening a Phage Display Library with Proteoliposomes Containing gp160

Figure 14B:
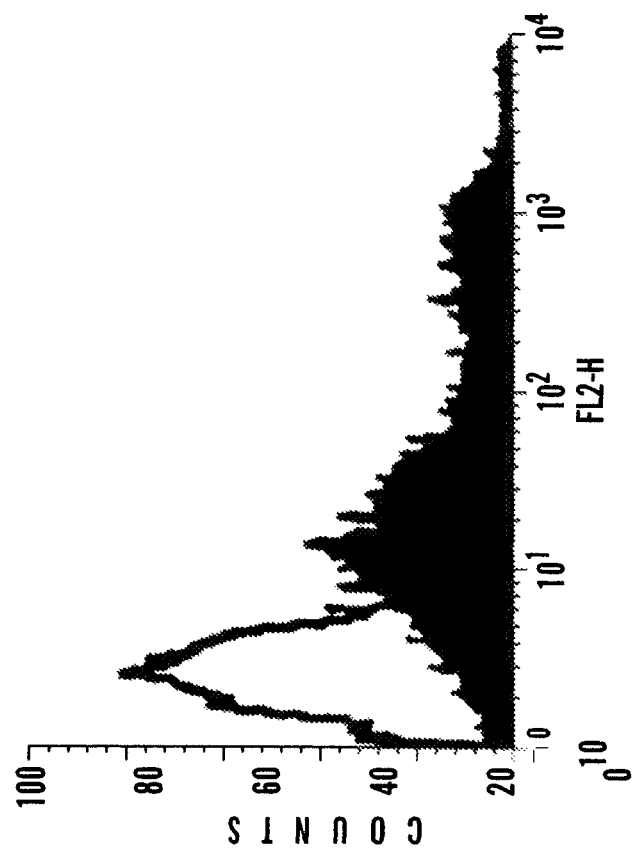
FIGS. 14A-B show FACS analysis of single-chain antibodies. Staining of 293T cells expressing gp160 is represented by the shaded peaks, and non-expressing control cells is represented by the unshaded peaks.
Figure 14A:
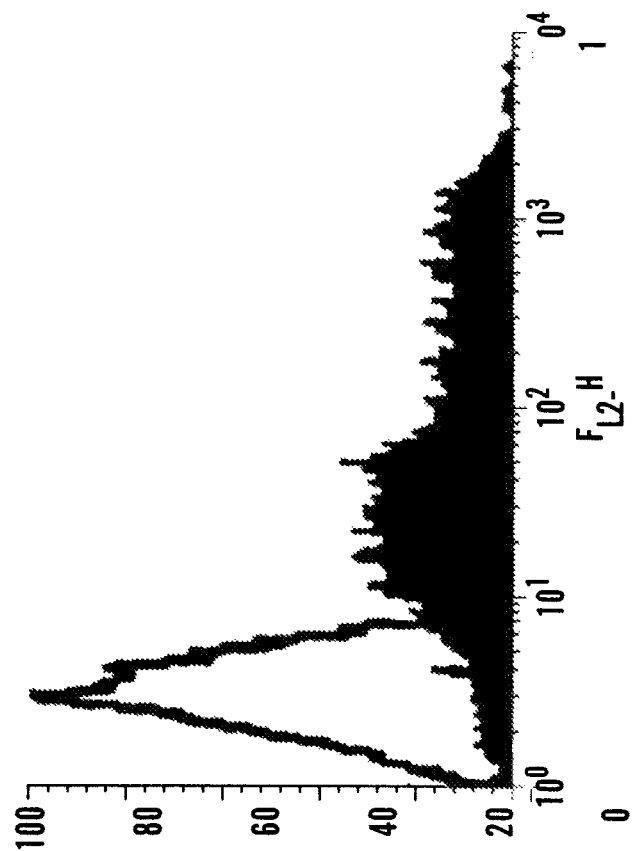

The defined, reconstituted gp160-proteoliposomes were used to pan a highly complex, human single-chain antibody phage display library generated in the laboratory of Dr. Wayne Marasco at the Dana-Farber Cancer Institute. After four rounds of panning, 96 clones were analyzed; 87 of the 96 clones were specific for gp120 as determined by ELISA (data not shown). The 9 non-reactive clones may represent oligomer specific antibodies or irrelevant reactivities. To confirm that the isolated phage possessed single-chain antibodies specific for gp160, FACS analysis was performed on cells expressing gp160 comparing anti-gp120 specific serum with the bacterial supernatant, an mouse anti-M13 phage IgG and anti-mouse-PE (FIG. 14). Further analysis of the soluble phage displayed single-chain antibodies is ongoing to determine their specificity. In any case, these intriguing preliminary data demonstrate the potential of the gp160-proteoliposomes to select and possibly elicit unique envelope-directed reactivities.

Example 5

Antibodies to Proteoliposomes Containing gp160

To confirm that the gp160 proteoliposomes could elicit envelope glycoprotein-specific antibodies, Balb/c mice were immunized IP with 5×10$^7$ proteoliposomes. By gel analysis, we estimated that each mouse received 1-2 µg of envelope glycoprotein per inoculation. To insure that the adjuvant would not disrupt the integrity of the reconstituted membrane, we preimmunized experimental mice IP with Ribi adjuvant 24 hours prior to inoculation of the beads. Subsequently we have performed membrane stability studies by incubation of rhodamine-DOPE-stained gp160 proteoliposomes in Ribi adjuvant for 2 and 24 hours. The beads were visualized by fluorescent microscopy and no decrease in the rhodamine-DOPE signal was observed on beads exposed to adjuvant (data not shown). Additional mice can be immunized with beads in Ribi adjuvant by various routes to optimize quantitative antibody responses.

Figure 15:
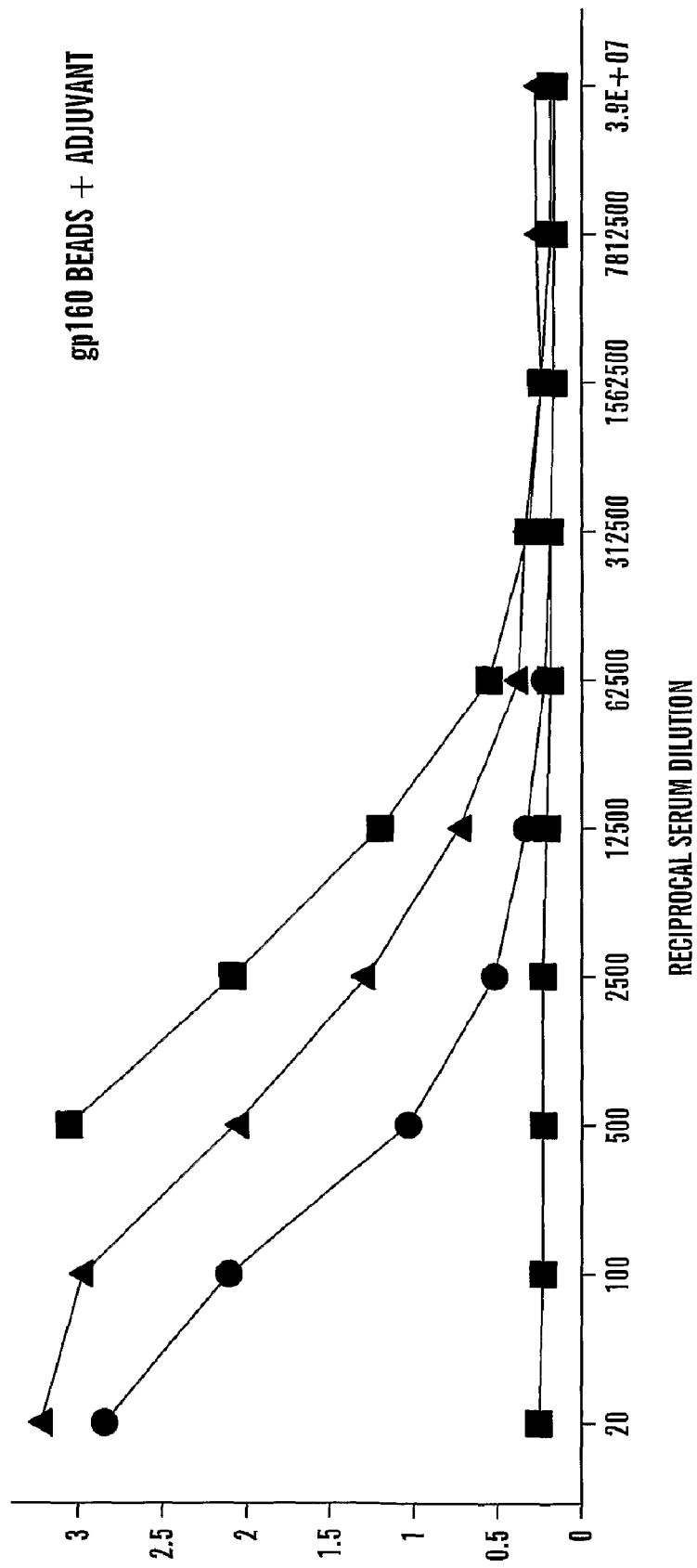
FIG. 15 shows an ELISA of sera from gp160 proteoliposome-immunized mice and control sera. Prebleed sera was used as negative control sera; PADRE serum refers to mice previously immunized with gp120-PADRE glycoproteins that served as a positive control.

For the initial study, 2 µg of monomeric YU2 gp120 in Ribi adjuvant was used as a positive control and membrane-reconstituted beads lacking gp160 glycoprotein were used as negative controls. After 3 inoculations, we have detected anti-gp120 antibodies in the sera of the mice from both the monomeric gp120 control group and the trimeric gp160 bead group, but not from the sera of negative control mice (FIG. 15). This study demonstrates the feasibility of utilizing the trimeric gp160 proteoliposomes as immunogens to better elicit neutralizing antibodies or elicit trimer-specific antibodies that can be isolated and characterized by monoclonal analysis. Such reagents are invaluable tools for the further elucidation of HIV-1 envelope glycoprotein higher-order structure.

Example 6

Proteoliposomes Containing gp120-gp41 Complexes

Figure 16:
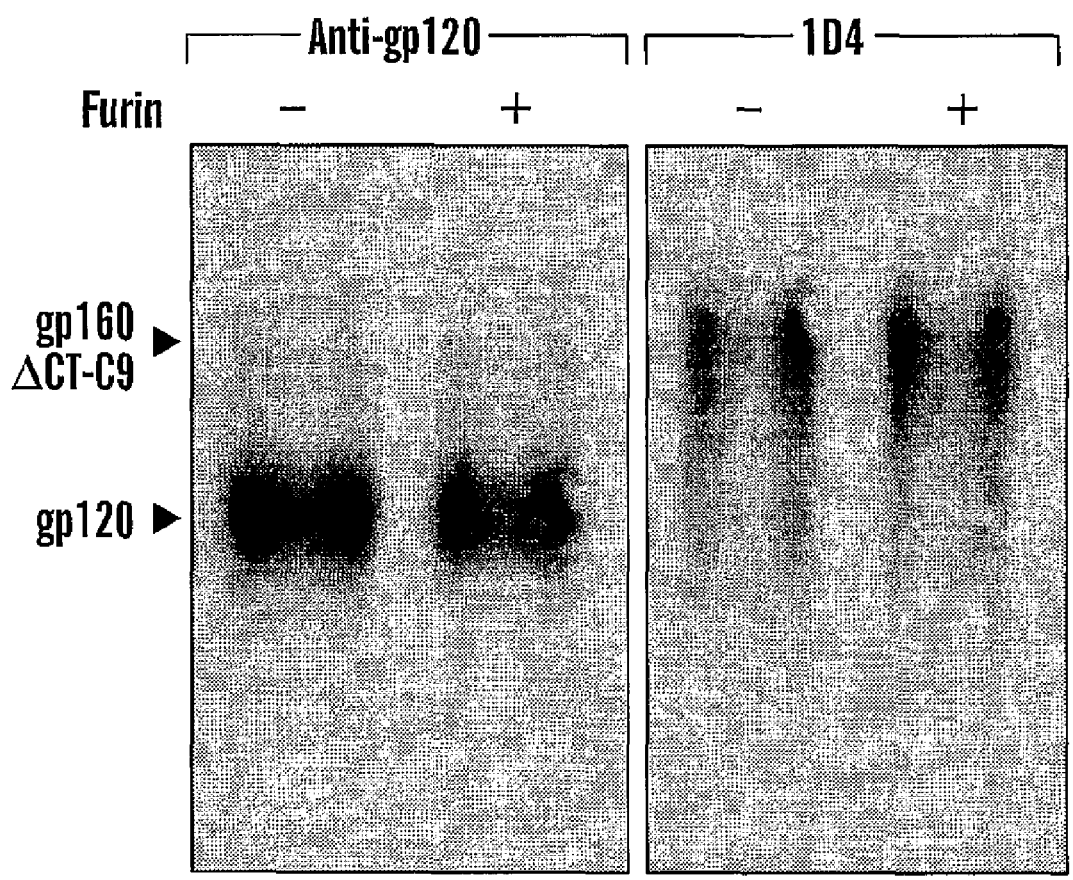
FIG. 16 shows retention of HIV-1 gp120-gp41 association in detergent lysates. The envelope glycoproteins from the 89.6 HIV-1 strain contain a deletion of the gp41 cytoplasmic tail and are tagged at the C-terminus with the C9 peptide epitope, which is recognized by the 1D4 antibody. The gp120-gp41 proteolytic cleavage site is intact in this construct. 293T cells were transfected with a plasmid expressing the 89.6 envelope glycoproteins, in some cases along with a plasmid expressing furin (189-192). The cells were lysed in buffer containing 1% CHAPSO, and the lysates incubated with 1D4 antibody-coated beads. After washing, the captured envelope glycoproteins were boiled off the beads and resolved on a 6% SDS-polyacrylamide gel. The gel was Western blotted and developed with a rabbit anti-gp120 serum and HRP-conjugated anti-rabbit IgG (left panel). The observed gp120 was precipitated by the 1D4 antibody through its association with gp41. The blot was then stripped and reprobed with the 1D4 antibody and HRP-conjugated anti-mouse IgG (right panel). Note that, in this example, the coexpression of furin did not significantly increase the amount of proteolytically processed envelope glycoproteins captured on the bead surface, probably because proteolytic cleavage is already very efficient in this context.

FIG. 16 shows retention of HIV-1 gp120-gp41 association in detergent lysates. The envelope glycoproteins from the 89.6 HIV-1 strain contain a deletion of the gp41 cytoplasmic tail and are tagged at the C-terminus with the C9 peptide epitope, which is recognized by the 1D4 antibody. The gp120-gp41 proteolytic cleavage site is intact in this construct. 293T cells were transfected with a plasmid expressing the 89.6 envelope glycoproteins, in some cases along with a plasmid expressing furin (189-192). The cells were lysed in buffer containing 1% CHAPSO, and the lysates incubated with 1D4 antibody-coated beads. After washing, the captured envelope glycoproteins were boiled off the beads and resolved on a 6% SDS-polyacrylamide gel. The gel was Western blotted and developed with a rabbit anti-gp120 serum and HRP-conjugated anti-rabbit IgG (left panel). The observed trimeric gp120 was precipitated by the 1D4 antibody through its association with gp41. The blot was then stripped and reprobed with the 1D4 antibody and HRP-conjugated anti-mouse IgG (right panel). Note that, in this example, the coexpression of furin did not significantly increase the amount of proteolytically processed envelope glycoproteins captured on the bead surface, probably because proteolytic cleavage is already very efficient in this context.

Example 7

Env-Proteoliposomes Elicit HIV-1 Envelope Glycoprotein Antibodies

Figure 17:
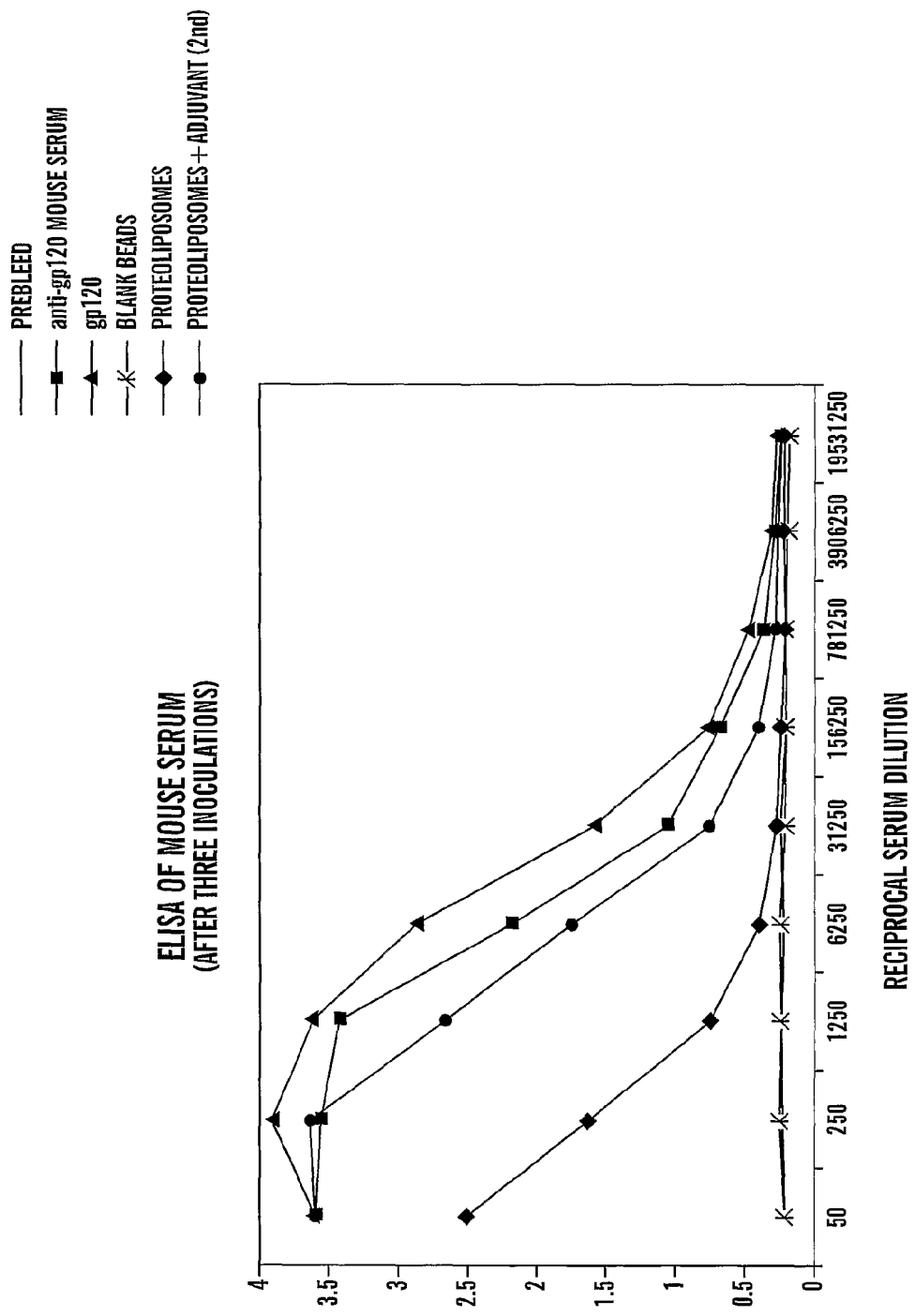
FIG. 17 shows immunization of mice with env-proteoliposomes. In a pilot study, four mice per group were immunized intraperitoneally (prime plus two boosts) with gp120 (in Ribi adjuvant), with Env-proteoliposomes alone, or with Env-proteoliposomes in Ribi adjuvant. The ability of the sera to recognize gp120-coated ELISA plates is shown. The ELISA was developed with horseradish peroxidase-conjugated anti-mouse IgG and optical density is indicated on the Y axis. Mean values are shown, and less than 30% deviation from the mean was observed in individual animals. The results indicate that proteoliposomes can elicit antibody responses to HIV-1 envelope glycoproteins, and that Ribi adjuvant can enhance those responses.

FIG. 17 shows immunization of mice with env-proteoliposomes. In a pilot study, four mice per group were immunized intraperitoneally (prime plus two boosts) with gp120 (in Ribi adjuvant), with Env-proteoliposomes alone, or with Env-proteoliposomes in Ribi adjuvant. The ability of the sera to recognize gp120-coated ELISA plates is shown. The ELISA was developed with horseradish peroxidase-conjugated anti-mouse IgG and optical density is indicated on the Y axis. Mean values are shown, and less than 30% deviation from the mean was observed in individual animals. The results indicate that proteoliposomes can elicit antibody responses to HIV-1 envelope glycoproteins, and that Ribi adjuvant can enhance those responses.

Figure 18:
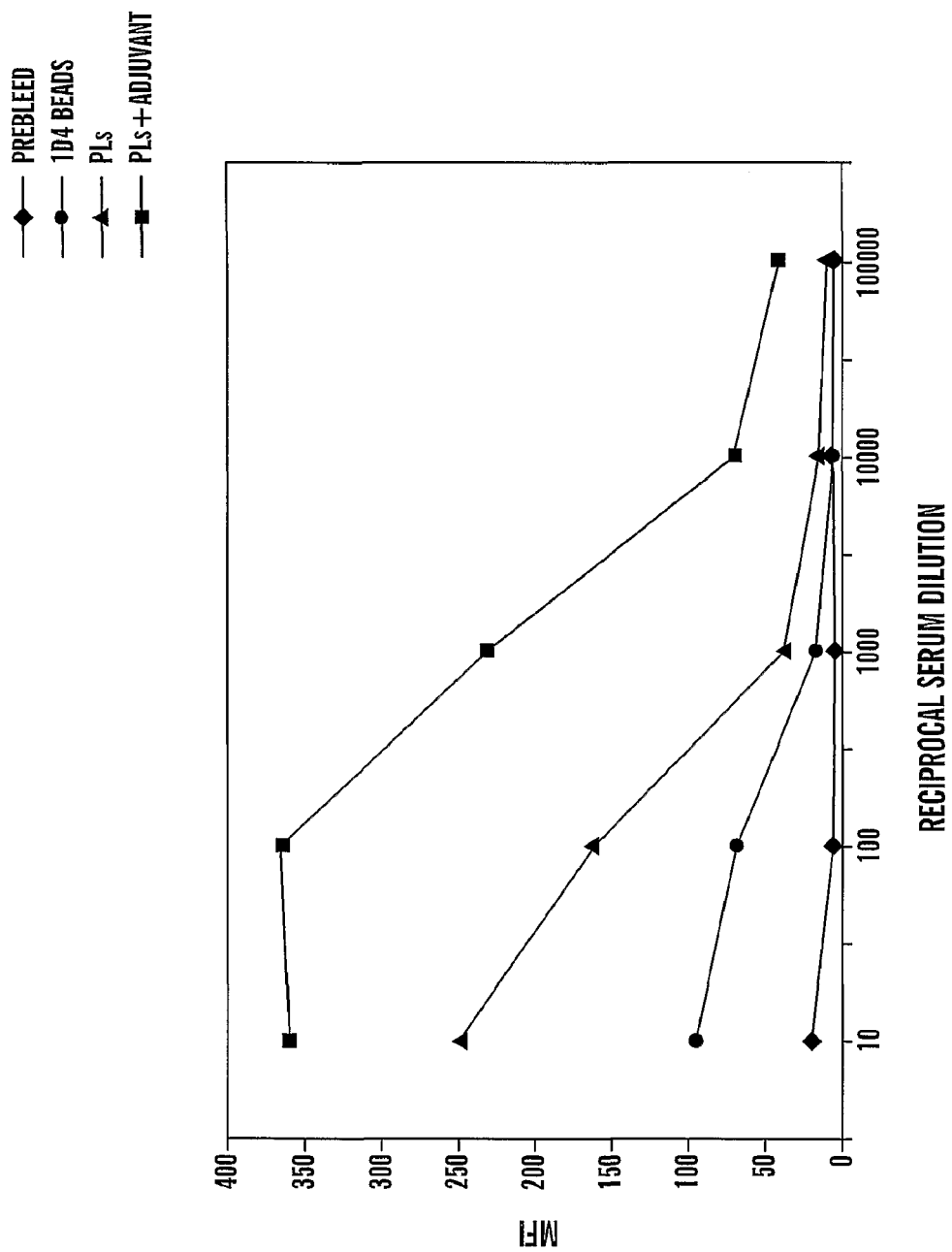
FIG. 18 shows that sera from mice immunized with env-proteoliposomes react efficiently with cell-surface HIV-1 envelope glycoproteins. Four mice per group were immunized intraperi-toneally with either Dynal beads coupled to the 1D4 antibody, Env-proteoliposomes alone, or Env-proteoliposomes in Ribi adjuvant. After priming and four boosts, the sera were tested for the ability to stain cells expressing the HIV-1 envelope glycoproteins of the same strain as the immunogen. The mean values for mean fluorescence intensity (MFI) are shown for each group of mice.

FIG. 18 shows that sera from mice immunized with env-proteoliposomes react efficiently with cell-surface HIV-1 envelope glycoproteins. Four mice per group were immunized intraperi-toneally with either Dynal beads coupled to the 1D4 antibody, Env-proteoliposomes alone, or Env-proteoliposomes in Ribi adjuvant. After priming and four boosts, the sera were tested for the ability to stain cells expressing the HIV-1 envelope glycoproteins of the same strain as the immunogen. The mean values for mean fluorescence intensity (MFI) are shown for each group of mice.

All references described herein are incorporated by reference.

We claim:

1. A method of obtaining an antibody to a viral envelope glycoprotein, the method comprising:
   (a) screening a library of antibodies with an immunogenic proteoliposome comprising:
      (i) a spherical or elliptoid shape having a ligand to a viral envelope glycoprotein anchored to the shape,
         wherein said shape's surface is surrounded by a lipid bilayer;
      (ii) said envelope glycoprotein bound to said ligand,
         wherein said envelope glycoprotein's transmembrane domain(s) are in said lipid bilayer and said envelope glycoprotein comprises a multimer containing two, three, or four monomeric units and has a wild-type conformation; and
      (iii) an attractant coating said shape's surface,
         wherein said lipid bilayer comprises a moiety that binds to the attractant forming a lipid bilayer surrounded shape; and
   (b) selecting antibodies in the library that bind to said proteoliposome.

2. The method of claim 1, wherein the avidity of the binding is further determined.

3. The method of claim 1, wherein the antibody is an antibody to an HIV-1 envelope glycoprotein.

4. The method of claim 3, wherein the envelope glycoprotein is an HIV-1 gp120 trimer, an HIV-1 gp160 trimer, a trimer of HIV-1 gp120 fragments, or a trimer of HIV-1 gp160 fragments.

5. The method of claim 1, wherein the attractant is streptavidin or avidin and the moiety is biotin.

6. The method of claim 1, wherein the ligand is an antibody.

7. The method of claim 1, wherein the envelope glycoprotein is a lentivirus envelope glycoprotein.

8. The method of claim 7, wherein the lentivirus glycoprotein is from HIV-1 or HIV-2.

* * * * *